US008274052B1

(12) United States Patent
Fukuzawa et al.

(10) Patent No.: US 8,274,052 B1
(45) Date of Patent: Sep. 25, 2012

(54) SPECIMEN IDENTIFICATION SYSTEM AND SPECIMEN IDENTIFICATION DEVICE

(75) Inventors: Hideaki Fukuzawa, Kawasaki (JP); Hiromi Yuasa, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/430,326

(22) Filed: Mar. 26, 2012

Related U.S. Application Data

(63) Continuation of application No. PCT/JP2009/066885, filed on Sep. 29, 2009.

(51) Int. Cl.
*G01J 5/02* (2006.01)

(52) U.S. Cl. ........... 250/341.1; 250/339.01; 250/339.11; 250/341.8; 250/358.1

(58) Field of Classification Search ............... 250/338.1, 250/338.4, 339.01, 339.02, 339.06, 339.11, 250/340, 341.1, 341.8, 358.1
See application file for complete search history.

(56) References Cited

U.S. PATENT DOCUMENTS

| | | | |
|---|---|---|---|
| 5,981,297 | A | 11/1999 | Baselt |
| 7,504,898 | B2 | 3/2009 | Fukuzawa et al. |
| 7,808,330 | B2 | 10/2010 | Fukuzawa et al. |
| 2008/0255006 | A1 | 10/2008 | Do |

FOREIGN PATENT DOCUMENTS

| | | |
|---|---|---|
| JP | 2005-172779 | 6/2005 |
| JP | 2006-153852 | 6/2006 |
| JP | 2007-10366 | 1/2007 |
| JP | 2007-71610 | 3/2007 |
| JP | 2007-124340 | 5/2007 |
| JP | 2009-70439 | 4/2009 |
| JP | 2009-98102 | 5/2009 |
| JP | 2009-158926 | 7/2009 |

OTHER PUBLICATIONS

M. Nagel, et al., "Integrated THz technology for label-free genetic diagnostics", Applied Physics Letters, vol. 80, No. 1, Jan. 7, 2002, pp. 154-156.

J.C. Slonczewski, "Current-driven excitation of magnetic multilayers", Journal of Magnetism and Magnetic Materials, vol. 159, 1996, pp. L1-L7.

S. I. Kiselev, et al., "Microwave oscillations of a nanomagnet driven by a spin-polarized current", Nature, vol. 425, Sep. 25, 2003, pp. 380-383.

International Search Report issued Oct. 27, 2009 in PCT/JP2009/066885 filed Sep. 29, 2009 (with English translation).

International Searching Authority Written Opinion mailed Oct. 27, 2009 in PCT/JP2009/066885 filed Sep. 29, 2009.

Toshihiko Onai et al., "Denso Senro o Mochiita Terahertz Shuseki Censer ni Kansuru Kenkyu", Extreme Photonics Kenkyu Extreme Nacho no Hassei to Oyo Dai 3 Kai Riken Bunshi Godo Symposium, 2006, pp. 85-86.

(Continued)

*Primary Examiner* — Mark R Gaworecki

(74) *Attorney, Agent, or Firm* — Oblon, Spivak, McClelland, Maier & Neustadt, L.L.P.

(57) ABSTRACT

In a specimen identification system, an oscillator directs a THz wave toward a channel that accommodates a specimen. A receiver detects the THz wave transmitted through the specimen. A first controller controls the oscillator to sweep the oscillation frequency of the THz wave within a frequency band. A receiver generates a receiving signal by sweeping the receiving frequency of the THz wave within the frequency band. A specimen identification unit specifies the specimen based on the waveform of the receiving signal within the frequency band.

10 Claims, 20 Drawing Sheets

OTHER PUBLICATIONS

T.Ohkubo, et al., "Micro-strip-line-based sensing chips for characterization of polar liquids in terahertz regime", Applied Physics Letters, vol. 88, 2006, pp. 212511-1-212551-3.

Ja-Yu Lu, et al., "Terahertz Microchip for Illicit Drug Detection", IEEE Photonics Technology Letters, vol. 18, No. 21, Nov. 1, 2006, pp. 2254-2256.

J.J. Baumberg, et al., "Ultrafast Coherent Spin Torques in Magnetic Quantum Wells", Springer Series in Chemical Physics, vol. 62, 1996, pp. 370-371.

M.A. Hoofer, et al., "Theory of Magnetodynamics Induced by Spin Torque in Perpendicularly Magnetized Thin Films", Physical Review Letters, Dec. 23, 2005, pp. 267206-1-267206-4.

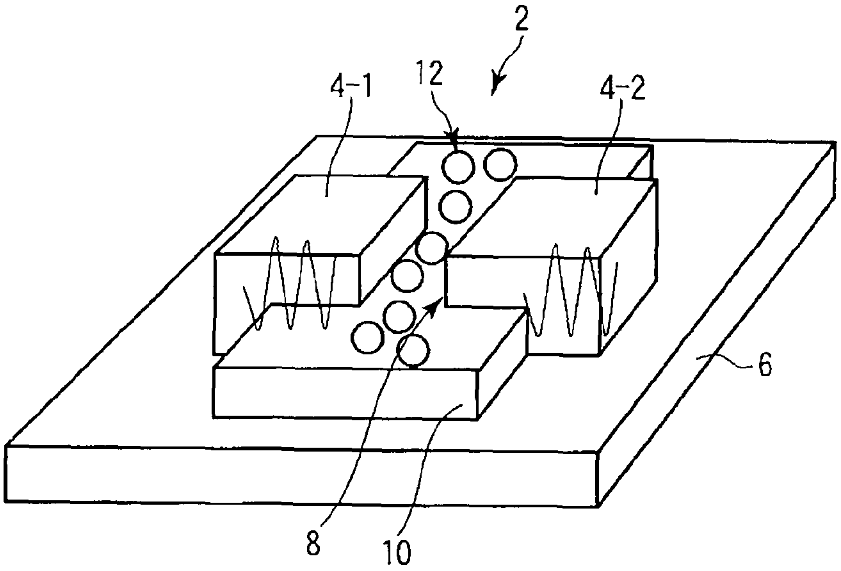
F I G. 2
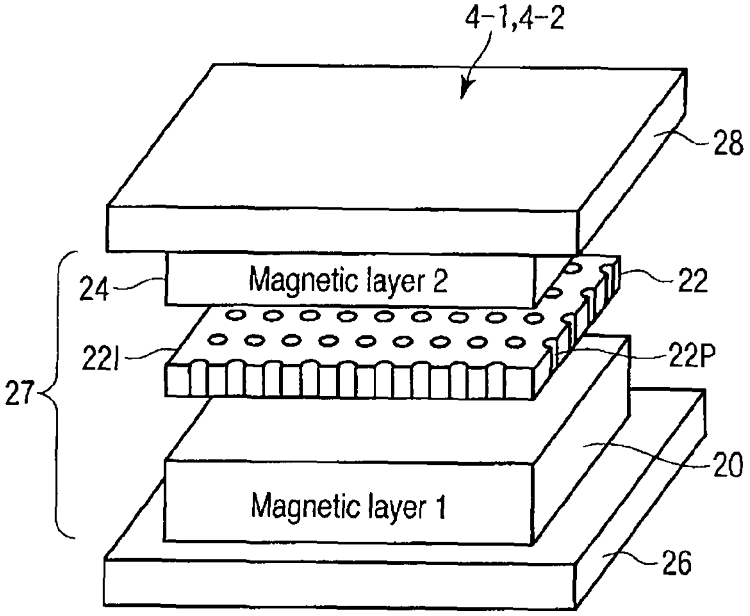
F I G. 3

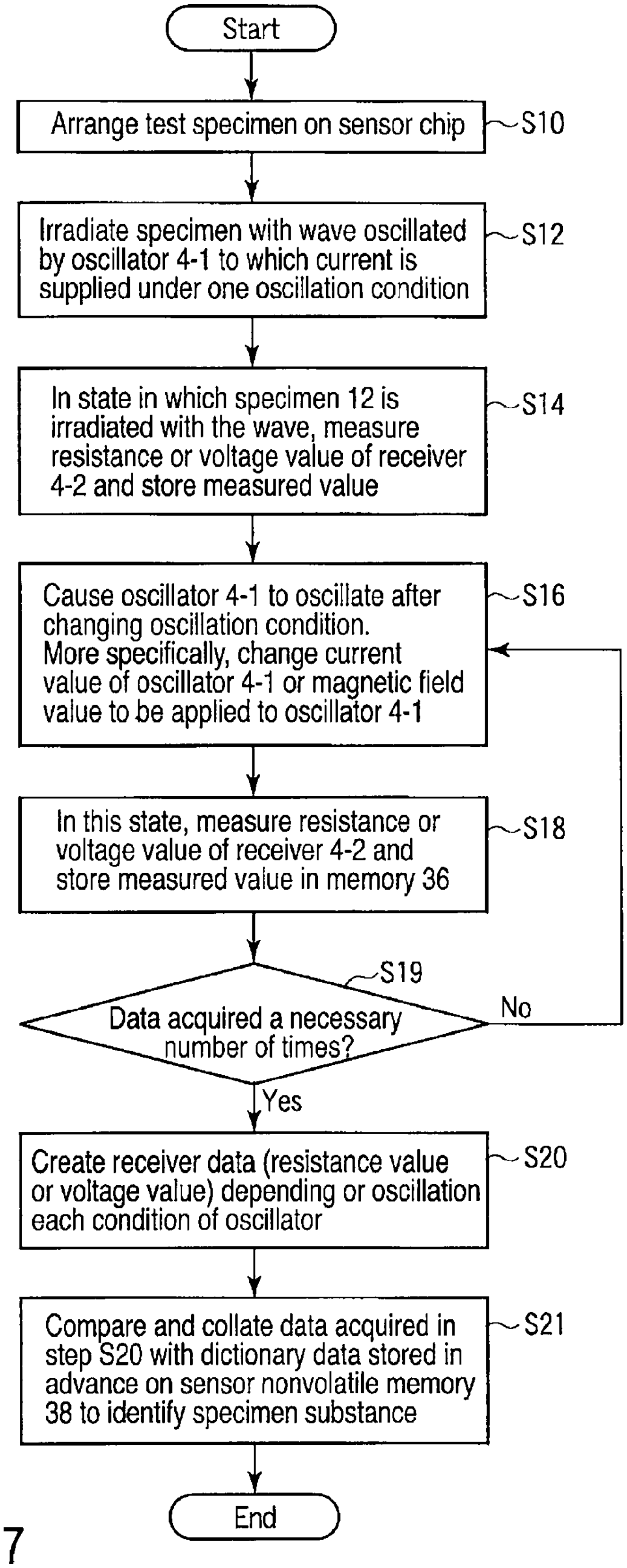
F I G. 7

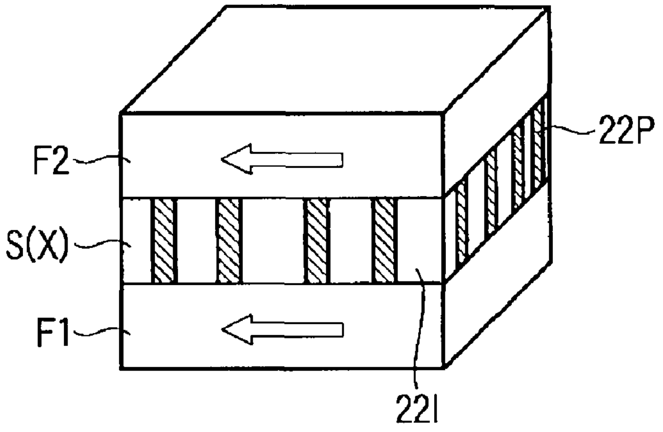
F I G. 8A
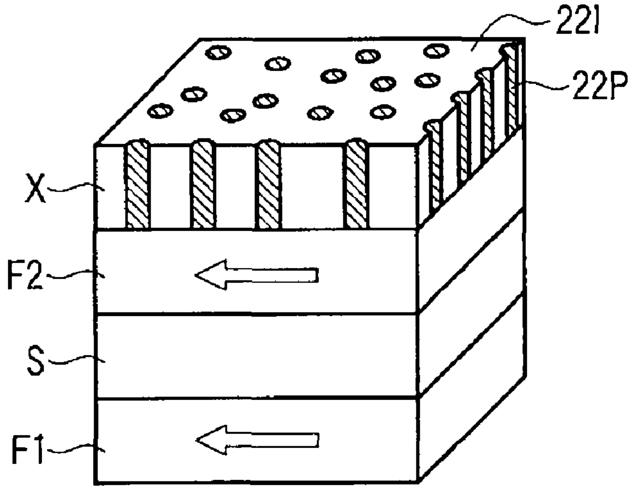
F I G. 8B

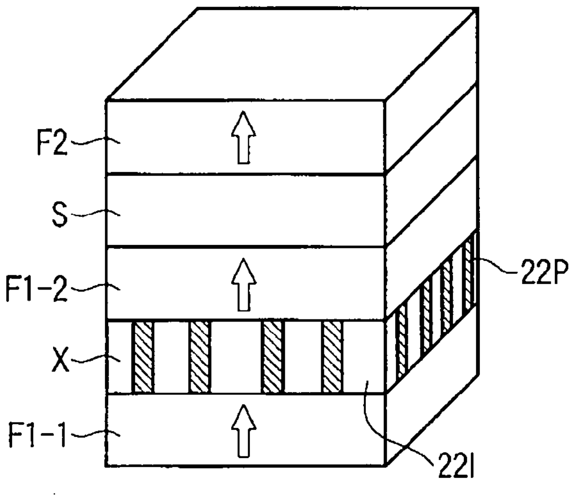
F I G. 10D
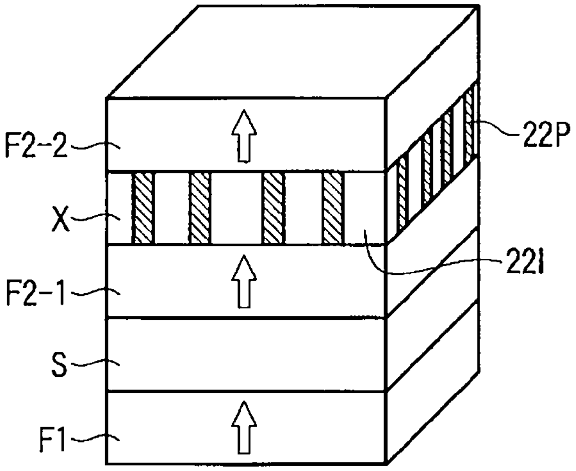
F I G. 10E

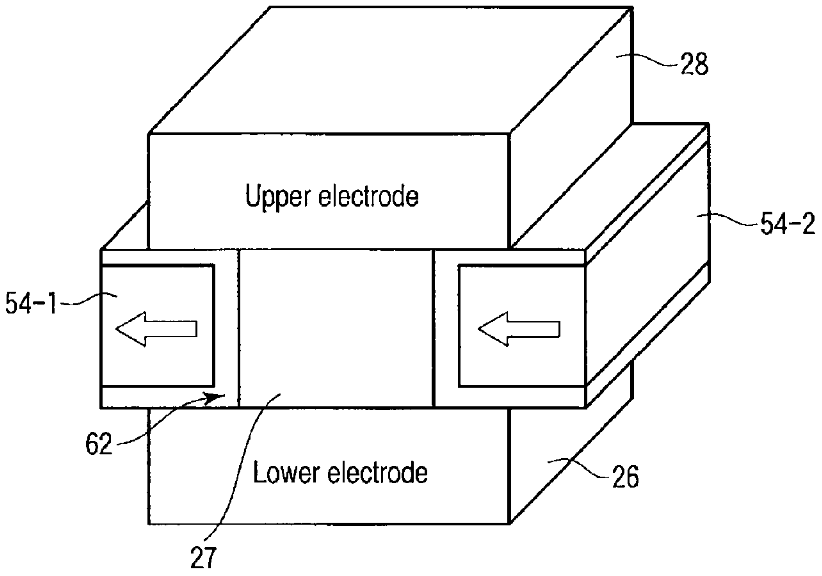
F I G. 13
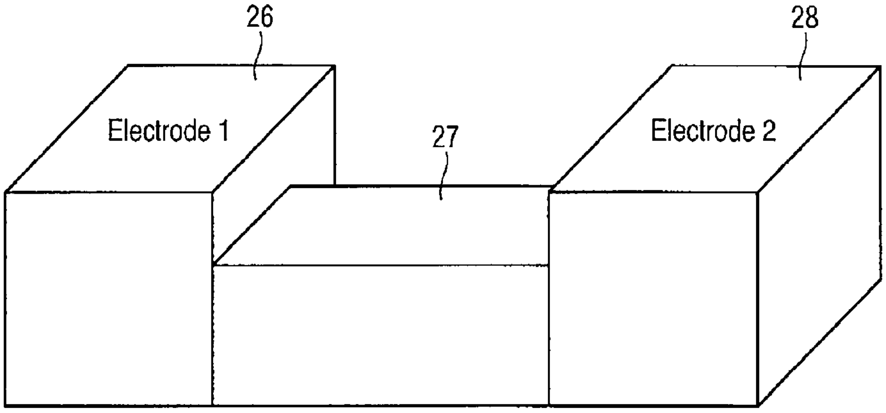
F I G. 14

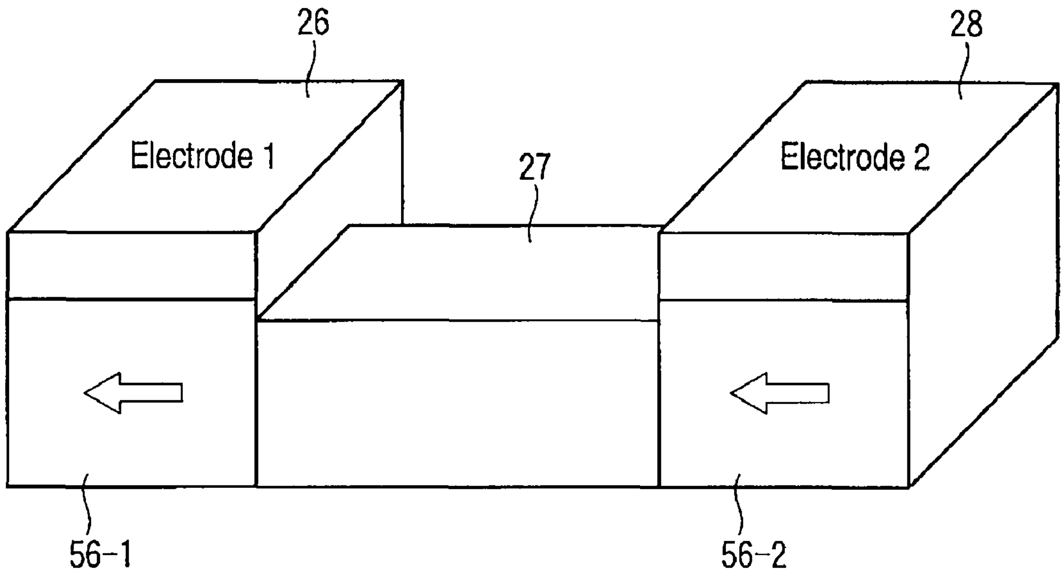
F I G. 15

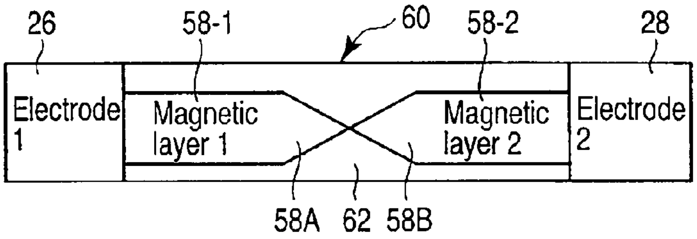
F I G. 16A
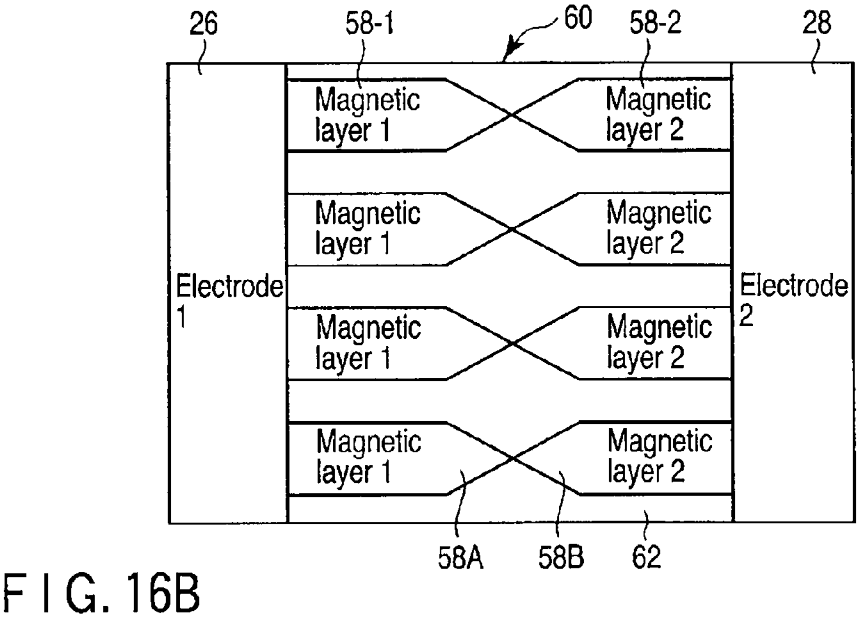
F I G. 16B
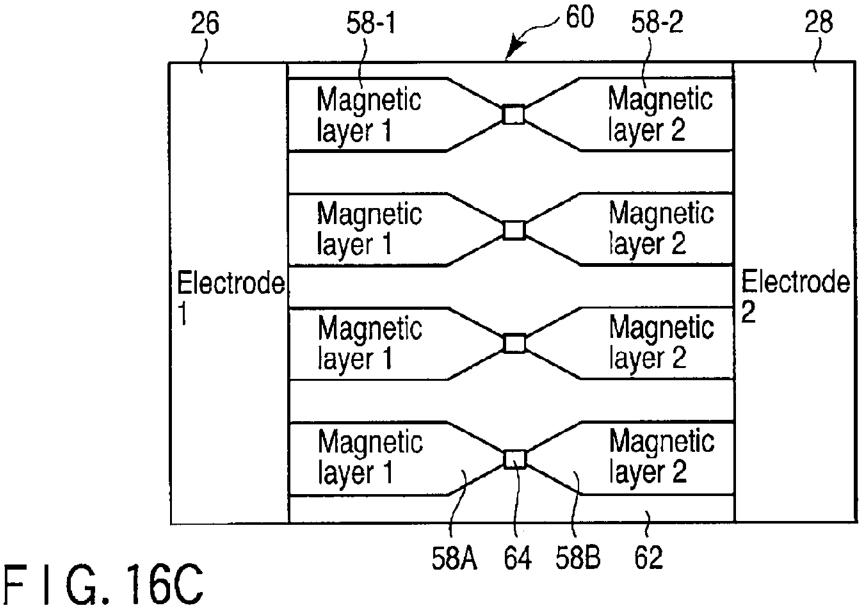
F I G. 16C

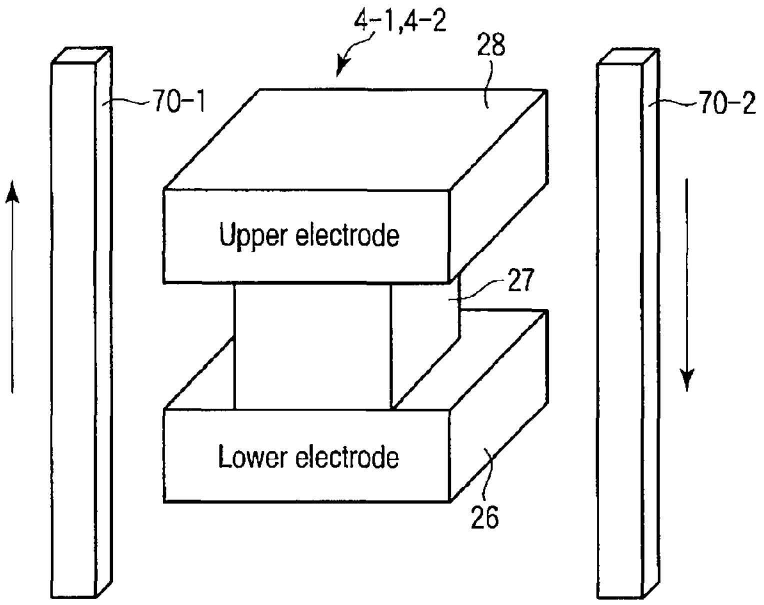
F I G. 17A
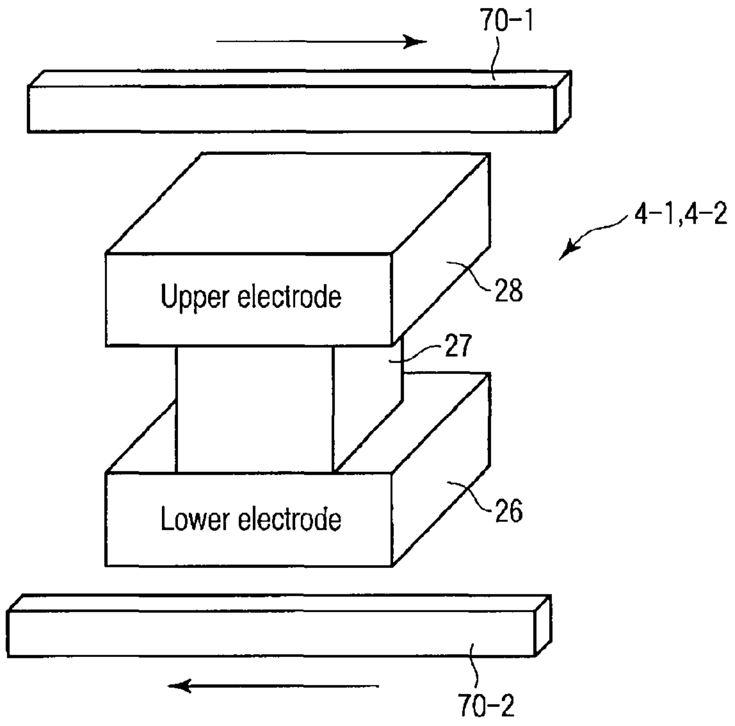
F I G. 17B

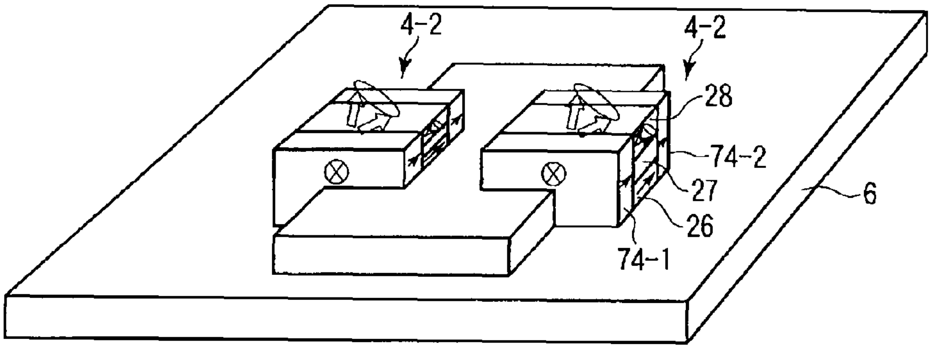
F I G. 20A
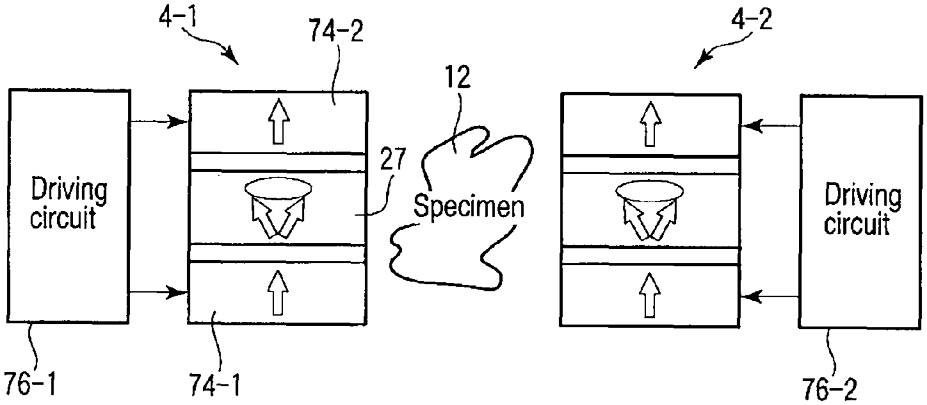
F I G. 20B

SPECIMEN IDENTIFICATION SYSTEM AND SPECIMEN IDENTIFICATION DEVICE

CROSS REFERENCE TO RELATED APPLICATIONS

This application is a Continuation Application of PCT Application No. PCT/JP2009/066885, filed Sep. 29, 2009, the entire contents of which are incorporated herein by reference.

FIELD

Embodiments described herein relate generally to a specimen identification device that irradiates a specimen with a wave and identifies the specimen based on the absorption spectrum or the reflection spectrum, and a specimen identification system comprising the specimen identification device.

BACKGROUND

Medical sophistication enables a higher level of medical treatment. However, advanced treatment for a serious disease is very expensive, and not everybody can afford it. Against this backdrop, there arises a need for preventive medicine and early disease detection that are easily available to everybody before large-scale treatment. Facilitating disease examination by a simpler test that is possible even at home makes it possible to detect a disease in its early stage and thus obtain a wide choice of options of medical operations and avoid the problem of high medical expenses.

However, relatively inexpensive tests as in today's physical checkups are not sufficient for discovery of serious diseases. It is more demanded to detect serious diseases at the inspection level of the physical checkup.

A biosensor has been studied as a device capable of implementing such a simple test in the future. There are various kinds and definitions of biosensors in this world. In this specification, the biosensor is defined as "a device that arranges a substance having biological information on a portable chip and performs some detection processing for the chip, thereby determining the biological information".

Such an ideal sensor is still in the research stage. Fundamental researches toward actualization include following related arts 1 to 3.

(Related Art 1: Label-Type Biosensor)

There is a specimen identification device such as a biosensor using magnetic beads to identify a specimen, which has been studied to identify a specimen, for example, a biological substance such as a protein or a DNA more easily than fluorometry currently in use. If a protein can easily be identified by a test on the chip, it may be possible to easily identify the biological substance at a clinic without using a bulky device. This specimen identification device features using the magnetic beads as a label in place of the conventional fluorescent substance. Detecting a magnetic field allows to perform specimen identification at a sensitivity higher than before. The conventional biosensor using magnetic beads as a label is known in U.S. Patent Application Publication 2008/0255006 and in D. R. Baselt, U.S. Pat. No. 5,981,297 (Nov. 9, 1999), "Biosensor using magnetically-detected label".

(Related Art 2: Label-Free Biospecimen Method)

As a medical determination technology that is an amalgam of state-of-the-art engineering and medical care, an attempt to obtain biological information without using a label by irradiating a biological substance with a special wave has been proposed in Appl. Phys. Lett. 80, 1, 154 (2002), "Integrated THz technology for label-free genetic diagnostics", JP-A 2006-153852 (KOKAI), and JP-A 2007-10366 (KOKAI).

(Related Art 3: Oscillator Using Spin Torque Effect)

As a device capable of oscillating a high frequency at room temperature, an STO (Spin Torque Oscillator) using the spin-torque effect has been proposed in J. C. Slonczewski, J. Magn. Magn. Mater. 159, L1 (1996), and a lot of theoretical and experimental examinations have been made. This document is known as the first paper that has introduced the basic concept. Actual experimental verifications have been done since then, in a document such as S. I. Kiselev et al, Nature 425, 308 (2003) and many groups following it to reveal that using the spin-torque effect allows to oscillate at a frequency of several GHz.

There is proposed a variation of the STO proposed in M. A. Hoefer et al, Phys. Rev. Lett. 95, 267206 (2005), "Theory of magnetodynamics induced by spin-torque in perpendicularly magnetized thin films", which readily oscillates by adopting a structure including a number of nano-size current path portions so as to improve the local current density.

The detection method using a label such as magnetic beads is too complex to enable early determination not in a large medical institution but at a simple clinic in town and in turn at home, and diagnosis at home is therefore very difficult. However, there is no label-free biosensor capable of easily doing specimen identification on a chip.

On the other hand, a label-free diagnosis method using THz waves exists. This method requires a bulky device to oscillate a THz wave, and diagnosis at home is more difficult than that using the biosensor using magnetic beads. That is, to allow diagnosis at home, a label-free specimen identification method is necessary. However, the THz wave suitable for label-free identification cannot be oscillated on a chip.

A GHz-order oscillator implementable on a chip exists as a conventional technique. However, implementation of THz oscillation is supposed to be difficult.

BRIEF DESCRIPTION OF THE DRAWINGS

FIG. 2 is a perspective view schematically showing the permeability detection type specimen identification device shown in FIG. 1.

FIG. 3 is an exploded perspective view schematically showing the structure of a receiver or an oscillator shown in FIG. 2.

FIG. 7 is a flowchart showing the identification procedure or sequence of the specimen identification system shown in FIG. 1.

FIG. 8A is a perspective view schematically showing the device structure shown in FIG. 3.

FIG. 8B is a perspective view schematically showing another example of the device structure shown in FIG. 3.

FIG. 10D is a perspective view schematically showing another modification of the device structure shown in FIG. 8D.

FIG. 10E is a perspective view schematically showing another modification of the device structure shown in FIG. 8E.

FIG. 13 is a perspective view schematically showing a modification of the structure of the receiver or the oscillator shown in FIG. 3 which comprises a magnetic field application mechanism.

FIG. 14 is a perspective view schematically showing another example of the structure of the receiver or the oscillator shown in FIG. 3.

FIG. 15 is a perspective view schematically showing still another example of the structure of the receiver or the oscillator shown in FIG. 3.

FIG. 16A is a plan view schematically showing the single layer structure of the receiver or the oscillator shown in FIG. 3 according to another embodiment.

FIG. 16B is a plan view schematically showing the single layer structure of the receiver or the oscillator shown in FIG. 3 according to still another embodiment.

FIG. 16C is a plan view schematically showing the single layer structure of the receiver or the oscillator shown in FIG. 16B according to a modification.

FIG. 17A is a perspective view schematically showing a structure according to another embodiment of the receiver or the oscillator shown in FIG. 3 which comprises a magnetic field application mechanism.

FIG. 17B is a perspective view schematically showing a structure according to still another embodiment of the receiver or the oscillator shown in FIG. 3 which comprises a magnetic field application mechanism.

FIG. 20A is a perspective view schematically showing a specimen identification device according to still another embodiment in which a receiver and an oscillator each comprising a magnet device for applying a magnetic field to the stacked structure are arranged on a substrate.

FIG. 20B is a plan view schematically showing a planar arrangement of the specimen identification device shown in FIG. 20A.

DETAILED DESCRIPTION

Figure 1:
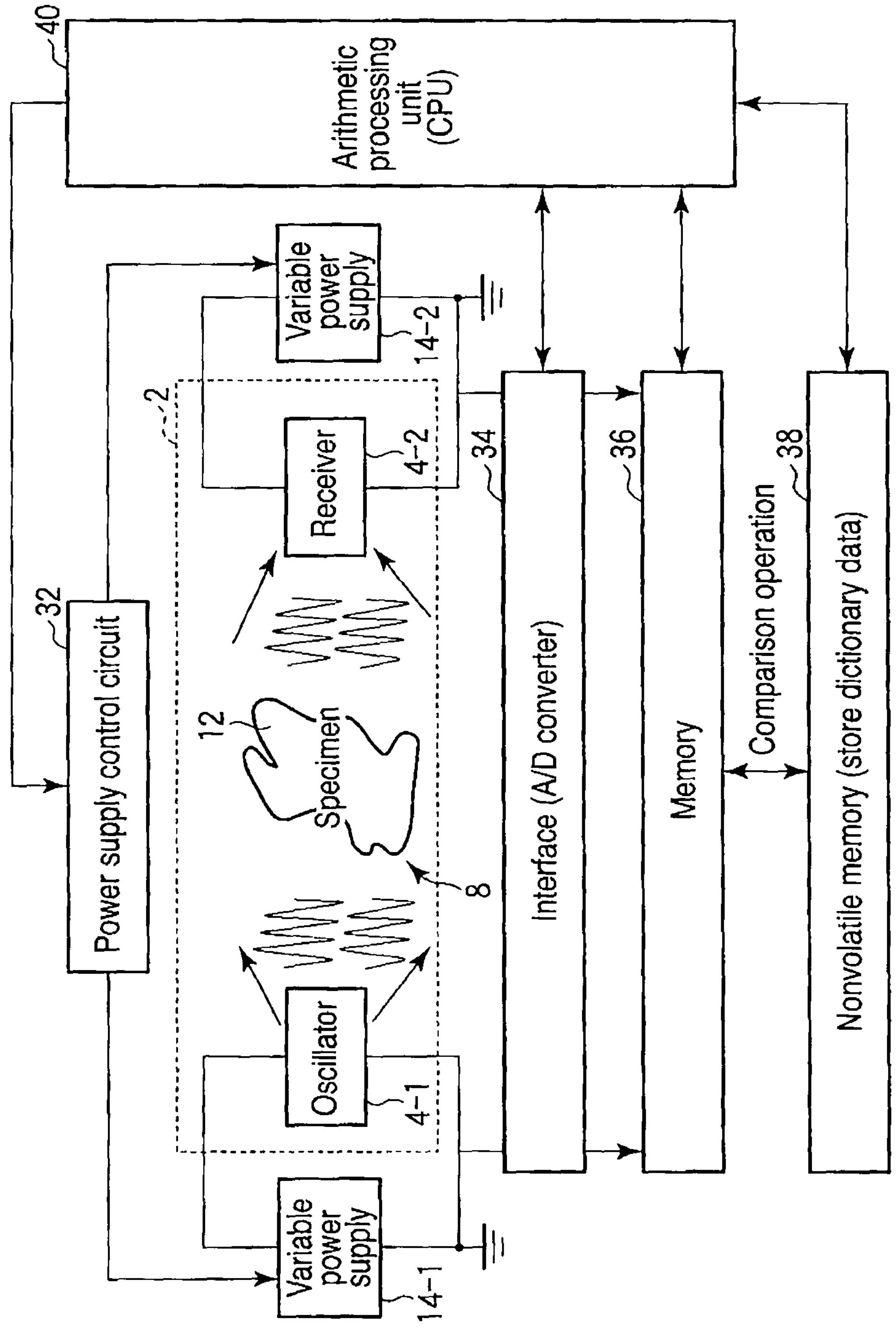
FIG. 1 is a block diagram showing a specimen identification system according to one embodiment which comprises a specimen identification device for identifying a specimen.

There will be described a specimen identification device and a specimen identification system for identifying a specimen according to an embodiment with reference to the accompanying drawings.

According to an embodiment, there is provided a specimen identification device comprising an oscillator that generates a THz wave, wherein the oscillator generates the THz wave by sweeping an oscillation frequency of the THz wave within a frequency band. In this embodiment, the THz wave means a wave having a frequency of 0.1 to 100 THz. The specimen identification device provided with a channel defining a waveguide to be irradiated with the THz wave, in which a specimen is accommodated. The specimen identification device provided with a detector (also called a receiver) that detects the THz wave transmitted through or reflected by the specimen, the detector generating a detection signal (also called a receiving signal) by sweeping a detection frequency of the THz wave within the frequency band. In this embodiment, the meaning of a word ‘detect’ corresponds to the meaning of a word ‘receive’.

In the specimen identification device, at least one of the oscillator and the detector is formed from a device having a stacked film structure including a first magnetic layer, an intermediate layer on the first magnetic layer, and a second magnetic layer on the intermediate layer.

According to another embodiment, there is provided a specimen identification system comprising a specimen identification device including an oscillator that generates a THz wave, a channel that defines a waveguide to be irradiated with the THz wave and accommodates a specimen, and a detector that detects the THz wave transmitted through or reflected by the specimen. The system further comprises an oscillation control unit that controls the oscillator, the oscillation control unit causing the oscillator to sweep an oscillation frequency of the THz wave within a frequency band, a detection driving unit that causes the detector to detect the THz wave, the detection driving unit generating a detection signal by sweeping a detection frequency of the THz wave within the frequency band, and a specimen identification unit that specifies the specimen based on a waveform of the detection signal within the frequency band.

According to the embodiment, it is possible to implement a biosensor that performs label-free specimen identification of a biological substance such as blood, a protein, a virus, a bacillus, a DNA, an RNA, a micro RNA, or an antibody. These biological substances can be obtained from blood, saliva, urine, feces, hair, sebum, and the like of a living body.

According to the embodiment, it is also possible to perform specimen identification at a sensitivity hither than before. In addition, since identification can be done much more easily than before, an individual can do it at home.

The device can serve not only as a biosensor but also as an environmental analysis sensor so that specimen identification can be done in a place close to the site without bringing analyzing a substance contained in water, atmosphere, or soil to a special laboratory. This enables quick feedback for environmental measures.

As the third classification, even in drug testing of chemicals, narcotics, or stimulants to be conducted in a quarantine station, a drug can easily be identified in the quarantine station before bringing it to a specific testing/analysis facility for drug identification. This allows to make a contribution to prevent harmful chemicals, narcotics, or stimulants from spreading in the society.

In the following explanation of the embodiment, the specimen identification device will be described together with its functions while placing focus on application of a biosensor. However, it is obvious that a specimen 12 to be identified by the specimen identification device need not always be a biological substance and may be an environmental substance or a drug, and the specimen identification device is applicable not only to a biosensor but also to an environmental analysis sensor and a drug testing sensor.

FIG. 1 shows the overall arrangement of a specimen identification system according to one embodiment which comprises a specimen identification device 2 for identifying the specimen 12. FIG. 2 shows the arrangement structure of the specimen identification device shown in FIG. 1. FIG. 3 is an exploded perspective view schematically showing the structure of a receiver or an oscillator shown in FIG. 2.

As shown in FIG. 2, the specimen identification device 2 comprises a substrate 6 made of a nonmagnetic material. An oscillator 4-1 and a receiver 4-2 are arranged on both sides of a channel 8 on the substrate 6 so as to face each other. The channel 8 serves as a waveguide to which a THz (terahertz) wave from the oscillator 4-1 travels. The THz wave passes through the channel 8 and travels toward the receiver. The oscillator 4-1 and the receiver 4-2 are formed in close vicinity to a frame 10 that is made of a nonmagnetic material to define the channel 8. The channel 8 between them is formed on the substrate 6 so as to have a gap length selected within the range of several ten μm to several cm in accordance with the specimen 12 to be identified. A protective film (not shown) made of a nonmagnetic material is preferably formed on each of the surfaces facing the oscillator 4-1 and the receiver 4-2. Instead of providing a protective film, the channel itself may be formed from a tube (not shown) to define a space or a channel closed with respect to the exterior, and the specimen 12 may float or be held on the channel 8 in the tube. As shown in FIG. 2, the specimen identification device 2 is preferably manufactured as an integrated circuit on the single substrate 6 as in a semiconductor manufacturing step.

The specimen identification device 2 is preferably provided on a chip indicated by the broken line in FIG. 1 so as to be electrically connectable to and mechanically detachable from the specimen identification system. The specimen identification device 2 formed on a chip has an airtight structure to prevent a specimen from leaking to the outside and is more preferably manufactured as a disposable device.

Molecules serving as the specimen 12 flow or are held on the channel 8, which can be resonated at a natural frequency in a measurement. The specimen 12 corresponds to biomolecules that make up a biological substance such as a protein, a virus, a bacillus, a DNA, an RNA, a micro RNA, or an antibody, as already described above. In addition, the specimen 12 can be assumed to be organic molecules or inorganic molecules of a substance contained in water, atmosphere, or soil. The specimen 12 can also be assumed to be molecules of a drug such as a chemical, a narcotic, or a stimulant to be detected in a quarantine station.

The specimen 12 itself may be mixed in a solution so as to float. However, the specimen 12 is preferably not mixed in an aqueous solution to obtain a higher measurement accuracy. Since the molecules of an aqueous solution hardly pass a THz wave, the signal detection accuracy for the specimen 12 in the receiver 4-2 lowers. From this viewpoint, the spatial area between the oscillator 4-1 and the receiver 4-2 is preferably shielded from the external environment so as not to contain water.

The oscillator 4-1 generates a THz wave toward the molecules of the specimen 12 in the channel 8. When the specimen 12 is irradiated with the THz wave corresponding to the natural frequency of the molecules of the specimen 12, the receiver 4-2 detects the wave that is modulated upon passing through the specimen. In this specification, the THz wave means a wave having a frequency of 0.1 to 100 THz. The oscillator 4-1 generates a wave for which a variable power supply (also called a first controller) 14-1 shown in FIG. 1 sweeps the THz frequency over time within the THz frequency band. The receiver 4-2 also operates such that a variable power supply (also called a second controller) 14-2 shown in FIG. 1 sweeps the frequency tuned within the THz frequency band.

As shown in FIG. 3, each of the oscillator 4-1 and the receiver 4-2 comprises a stacked structure 27 between a lower electrode 26 and an upper electrode 28. The stacked structure 27 includes a magnetic layer 20 serving as a magnetization fixed layer (pinned layer) in which the direction of magnetization is fixed almost in one direction, an intermediate layer 22 stacked on the magnetic layer 20, and a magnetic layer 24 stacked on the intermediate layer 22 (spacer layer). A first metal layer (not shown) may be inserted between the magnetic layer 20 and the intermediate layer 22. A second metal layer (not shown) may be inserted between the magnetic layer 24 and the intermediate layer 22. The intermediate layer 22 has current paths 22P that extend through an insulating layer 22I along the direction of its thickness. Each current path (metal path) 22P is made of a metal having a diameter on the nanometer order. More specifically, the current path (metal path) 22P is made of a magnetic material such as Fe, Co, or Ni or a nonmagnetic material such as Cu, Au, Ag, or Al having a diameter on the nanometer order. In some cases, the magnetic layer 20 is mounted and fixed on an underlying layer and a pinning layer (neither are shown) on the lower electrode 26. In this case, the magnetic layer 20 has a stacked structure including a lower pinned layer stacked on the pinning layer, an Ru layer, and an upper pinned layer in contact with the intermediate layer 22. The magnetic layer 24 is formed under a cap layer (not shown) under the upper electrode 28. In the oscillator 4-1, the magnetic layer 24 is called a magnetic oscillation layer and oscillates a wave having a frequency in the THz band. More specifically, assume that a current flows between the lower electrode 26 and the upper electrode 28 in a direction perpendicular to the film planes of the stacked film including the magnetic layer 20, the intermediate layer 22, and the magnetic layer 24. The current is confined in the current paths 22P of the intermediate layer 22. In this state, electrons are injected into the other magnetic layer. Spin wave excitation (precession of magnetization) occurs in the magnetic layer 24 serving as the magnetic oscillation layer due to spin transfer torque in the high current density state caused by the constructed current, and a wave having a frequency in the THz band is oscillated. The oscillation frequency of the wave is determined by the value of the direct current (DC current) supplied between the lower electrode 26 and the upper electrode 28. The oscillation frequency of the wave to be output from the oscillator 4-1 can be changed within the THz frequency band by decreasing or increasing the DC current. When the current increases, the oscillation frequency rises. Referring to FIG. 1, the variable power supply 14-1 and a power supply control unit 32 that controls the variable power supply 14-1 constitute an oscillation control unit that controls the current to the oscillator 4-1. The oscillator 4-1 oscillates while sweeping the oscillation frequency of the THz wave within a frequency band.

The oscillator 4-1 is called a CCP-CPP oscillator (Current-Confined-Path Current-Perpendicular-To-Plane (CPP) Oscillator) because the current path is confined on the nanometer order.

For further information of the CCP-CPP oscillator, see patent literature 4 to be described below. The described contents of patent literature 4 can be incorporated in and constitute a part of the specification of this application.

The present inventors did not notice the CCP-CPP oscillator oscillating a THz wave at first, and reached a conclusion that THz wave oscillation is possible because of the following theoretical reason. That is, the present inventors have gotten an idea that the CCP-CPP oscillator can generate a wave having a frequency in the THz band, and the oscillation frequency of the wave to be output from the oscillator 4-1 can be changed within the THz frequency band by decreasing or increasing the DC current.

The reason for this idea will be described below.

Figure 4:
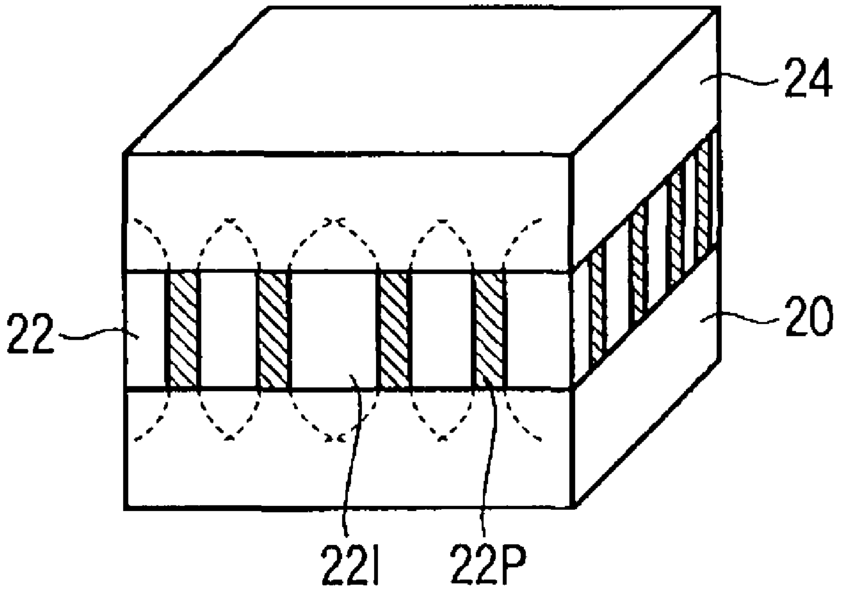
FIG. 4 is a schematic view for explaining current confinement in the device structure shown in FIG. 3.

In the CCP-CPP oscillator, the current is confined in the current paths of the intermediate layer 22, and the local current density is very high. The high current density enables to efficiently cause oscillation. FIG. 4 conceptually illustrates the local current concentration.

In the device structure of the oscillator 4-1 and the receiver 4-2, the upper electrode 28 and the lower electrode 26 are provided to supply the current to the magnetic multilayered film in the direction perpendicular to the film planes. However, FIG. 4 illustrates the device structure without the upper electrode 28 and the lower electrode 26 for the sake of simplicity, and the current distribution in this device structure. Referring to FIG. 4, the current distribution is indicated by broken lines and hatching. As shown in FIG. 4, the current supplied from one of the upper electrode 28 and the lower electrode 26 to the magnetic multilayered film in the direction perpendicular to the film planes is confined in the nano-size current paths 22P of the intermediate layer 22 and flowed toward the other electrode to generate a THz wave. Since the plurality of nano-size current paths 22P are provided, it is possible to efficiently cause high-frequency oscillation by spin torque at an oscillation frequency in a frequency domain higher than before.

FIG. 4 shows an example in which the CCP is used in the spacer layer between the two magnetic layers. A structure having the CCP inserted in the first or second magnetic layer is almost the same as described above. Hence, the structures of other examples shown in FIGS. 8A to 10E can also implement the same effect, as will be described later.

The effect of the local large current concentration results from the same physical effect as described in JP-A 2007-124340 (Kokai). When making the conception of the present embodiment, the present inventors have noticed that another unexpected phenomenon that is not described in JP-A 2007-124340 (Kokai) may occur due to the above-described phenomenon. More specifically, in the structure in which a lot of efficient oscillation portions having such a high current density are provided in vicinity, like the CCP-CPP oscillator, the waves generated by the respective CCPs interfere with each other between the CCPs in vicinity. This interference induces a special spin wave mode. The special spin waves raise the oscillation frequency. This effect is completely different from that obtained by the attempt to raise the oscillation frequency by simply reducing the size of the nano-size current path, as described in M. A. Hoefer et al, Phys. Rev. Lett. 95, 267206 (2005), "Theory of magnetodynamics induced by spin-torque in perpendicularly magnetized thin films". For this reason, there is a possibility that an oscillation frequency of 1 THz or more is implemented as the spin wave interference effect near the plurality of CCPs. The oscillation frequency is assumed to change in accordance with the CCP size, as a matter of course. However, according to the above-described concept, even if the CCP size does not change, the oscillation frequency changes depending on the distance design between the CCPs. That is, the oscillation frequency may rise due to the spin wave interference effect. The relationship between the CCP size and the value of the oscillation frequency depending on the distance between the CCPs is complex, and numerical calculation is necessary for its details. In any case, it is an important point that the oscillation frequency changes due to the interaction between the plurality of nano-size current paths in the CCP-CPP oscillator.

As another effect of the CCP-CPP device, since the number of nano-size current paths increases, and the oscillation region of the magnetic layer becomes large, the oscillation output can be expected to increase. This effect is the same as that described in JP-A 42007-124340 (Kotai). In a normal STO, the oscillation output is generally small. Hence, the increase in the oscillation output of the CCP-CPP device is one of the large effects advantageous for practical use.

When a high-density current is supplied to the overall device that has no CCP structure but includes, as a spacer layer, a Cu spacer layer, as described in S. I. Kiselev et al, Nature 425, 308 (2003), or an MgO tunnel barrier layer mentioned in many reports to obtain a high current density, the entire device may be heated, and the elements may diffuse, or the device may be molten. In addition, since oscillation occurs all over the film, there is no interaction between oscillation portions, and no special spin waves are generated, unlike the CCP-CPP device of the present concept of the embodiment. For this reason, it is quite impossible to implement an oscillation frequency on the THz order. In the CCP-CPP oscillator, however, since the current density rises locally, the heat is dissipated around the CCPs. Hence, neither element diffusion nor device melt occurs.

In a structure in which only one nano-size current path is formed, as disclosed in M. A. Hoefer et al, Phys. Rev. Lett. 95, 267206 (2005), "Theory of magnetodynamics induced by spin-torque in perpendicularly magnetized thin films", no spin wave mode between CCPs is formed, and only an oscillation phenomenon caused by one hole occurs. In this structure, no THz wave of 0.2 THz or more is oscillated. The upper limit of the oscillation frequency is very low, and the oscillation output is small.

Detailed examples of materials and film thicknesses will be described below with reference to the structure shown in FIG. 3 as an example. Each of the first magnetic layer 20 and the second magnetic layer 24 is formed from a magnetic layer including Fe, Co, Ni, or the like, and its film thickness is supposed to range from about 1 nm to 30 nm. Out of the spacer layer 22, the insulating layer 22I can be made of an oxide or nitride of Al, Zr, Mg, Hf, Si, Ta, Ti, Cr, W, Mo, Mn, Fe, Co, Ni or the like. The nano-size current paths 22P are supposed to be made of a metal material capable of passing a current. Detailed examples are materials such as Cu, Au, Ag, and Al capable of producing the conventional MR effect and magnetic element materials such as Fe, Co, and Ni. The metal material as described above is preferable. A noble metal layer material such as Pt, Pd, Ru, or Ir may also be used depending on the circumstances. The film thickness of the spacer layer 22 is supposedly defined to about 1 to 5 nm.

Note that the oscillator 4-1 formed from a THz light oscillation device and the receiver 4-2 formed from a receiving device are arranged on a single chip, thereby implementing the specimen identification device. As another characteristic feature of the embodiment except those described above, the detailed receiving means is solved by using, as the receiving device, a CCP-CPP device whose structure is almost the same as that of the oscillator. THz wave detection can be performed using the CCP-CPP device having the same structure as that of the oscillator without using any special detection system unique to THz waves.

When the receiver 4-2 has the stacked structure as shown in FIG. 3, the THz wave that has arrived from the oscillator 4-1 through the specimen is guided into the stacked structure of the receiver 4-2. A current is supplied between the lower electrode 26 and the upper electrode 28 of the receiver 4-2 in synchronism with the current supplied to the oscillator 4-1. The voltage is measured from the internal resistance generated between the lower electrode 26 and the upper electrode 28. When the specimen 12 is irradiated with a THz wave corresponding to the natural frequency of the molecules of the specimen 12, the wave that is modulated upon passing through the specimen is introduced into the receiver 4-2 and changes the internal resistance. The substance of the specimen 12 is specified based on the relationship between the resistance change and the resonance frequency.

The above principle or concept will be described below in more detail. First, to cause the oscillator 4-1 to continuously oscillate THz waves, a current having a fixed current value is supplied to it. The oscillation frequency changes depending on the value of the supplied current, as will be described later. The oscillation frequency changing depending on the current value is a characteristic feature common to oscillators using a magnetic multilayered film. The present features implementing this characteristic in a THz band of 0.1 THz or more. The oscillator 4-1 oscillates at the current value in accordance with the current supply and outputs a wave having an amplitude ($A=A_a$1) and a frequency ($f=f_a$1). The THz wave irradiates the specimen 12, and the receiver 4-2 detects the transmitted or reflected wave. In the arrangement of the oscillator 4-1 and the receiver 4-2 shown in FIG. 2, the receiver 4-2 detects the transmitted wave. When the specimen 12 is irradiated with a wave, both the amplitude and the frequency of the THz wave output from the oscillator 4-1 may change due to the influence of the natural frequency of the specimen 12. Let ($A=A_0^1$, $f=f_0$1) be the amplitude and frequency after passing through the specimen.

To cause the receiver 4-2 to detect the state in which the THz wave passes through the specimen 12, and both the amplitude and frequency ($A=A_0$1, $f=f_0$1) change, the value of the current to be supplied to the receiver 4-2 is swept and thus changed continuously or stepwise. When the oscillation frequency of the receiver 4-2 has become close to the frequency $f=f_0$1 in accordance with the change of the current value to the receiver 4-2, the THz wave that has arrived from the specimen 12 most interferes with the oscillation state of the receiver 4-2, and the characteristic of the receiver 4-2 changes. The degree of change depends on the amplitude of the THz wave transmitted through the specimen 12. Hence, the receiver 4-2 detects information of the amplitude $A_0^1$, too, because the amplitude $A_0^1$ affects the receiver 4-2. On the other hand, if the changed oscillation frequency of the receiver 4-2 is quite different from the frequency $f=f_0$1, the oscillation state of the receiver 4-2 is not affected at all and completely equals the state in which the transmitted wave from the specimen 12 does not enter the receiver 4-2. When oscillation of the receiver 4-2 is affected, the direction of magnetization in the oscillating magnetic layer of the receiver 4-2 is changed. This is because oscillation is caused by the change in the angle of magnetization in the magnetic layer. That is, the internal resistance of the receiver 4-2 changes as the relative angle of magnetization between the magnetization fixed layer and the oscillating layer changes. This is because the value of the resistance of the device changes depending on the relative angle between magnetic layer 1 and magnetic layer 2. In FIG. 3, both the first magnetic layer 20 and the second magnetic layer 24 can be the oscillating layer. When the first magnetic layer 20 is the magnetization fixed layer, the second magnetic layer 24 is the oscillating layer. When the direction of magnetization in the oscillating layer changes due to the THz wave from the specimen, it can be read as the resistance change or voltage change in the receiver 4-2. This is equivalent to detecting a resistance change using the magnetoresistive effect such as the GMR effect or TMR effect. The resistance change can be read as a voltage change because a sense current is supplied.

Referring to FIG. 1, a variable power supply 14-2 and the power supply control unit 32 that controls the variable power supply 14-2 constitute a detection driving unit that drives the receiver 4-2 to detect a THz wave. The detection driving unit drives the receiver 4-2 and sweeps the detection frequency of the THz wave within a frequency band, thereby causing the receiver 4-2 to oscillate and generate a detection signal.

Figure 5:
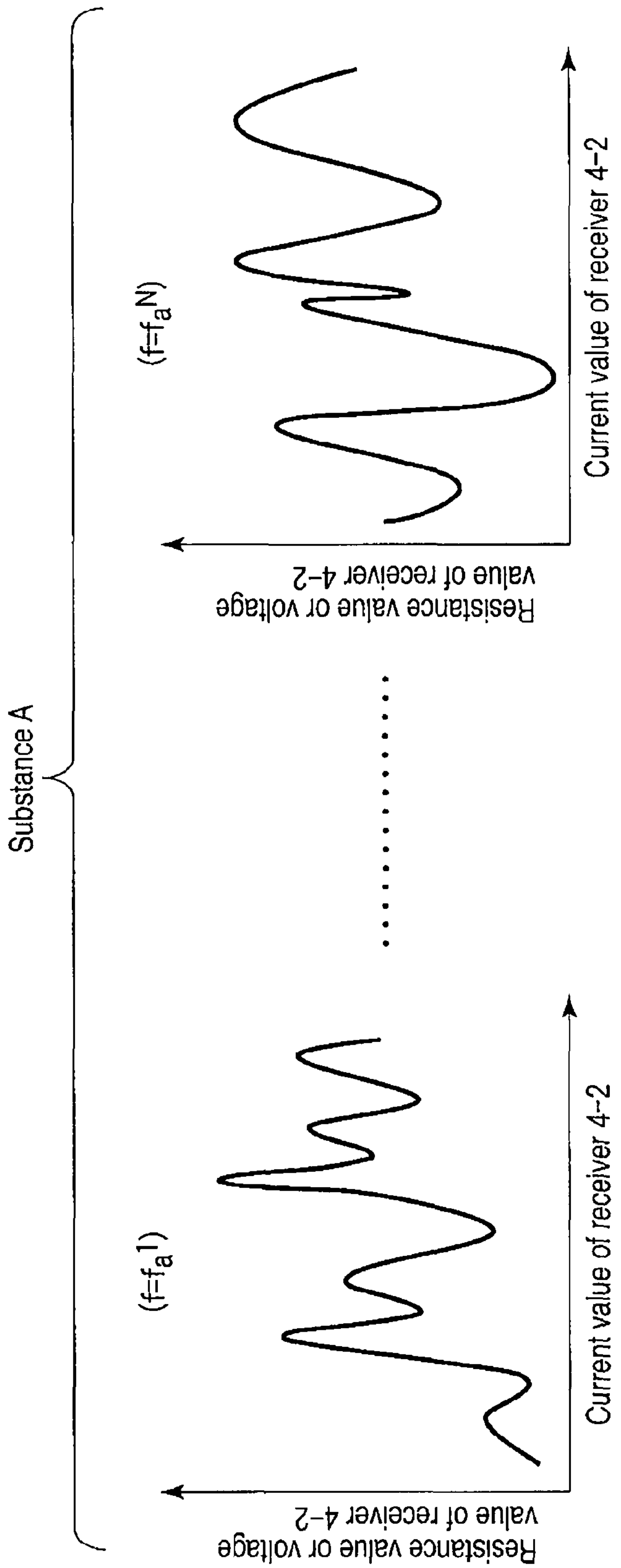
FIG. 5 illustrates graphs showing an example of detected data to be compared with dictionary data concerning a substance A which is detected by the receiver in correspondence with oscillation frequencies $f_a$1 to $f_a$N of waves oscillated by the oscillator in the specimen identification system shown in FIG. 1.
Figure 6:
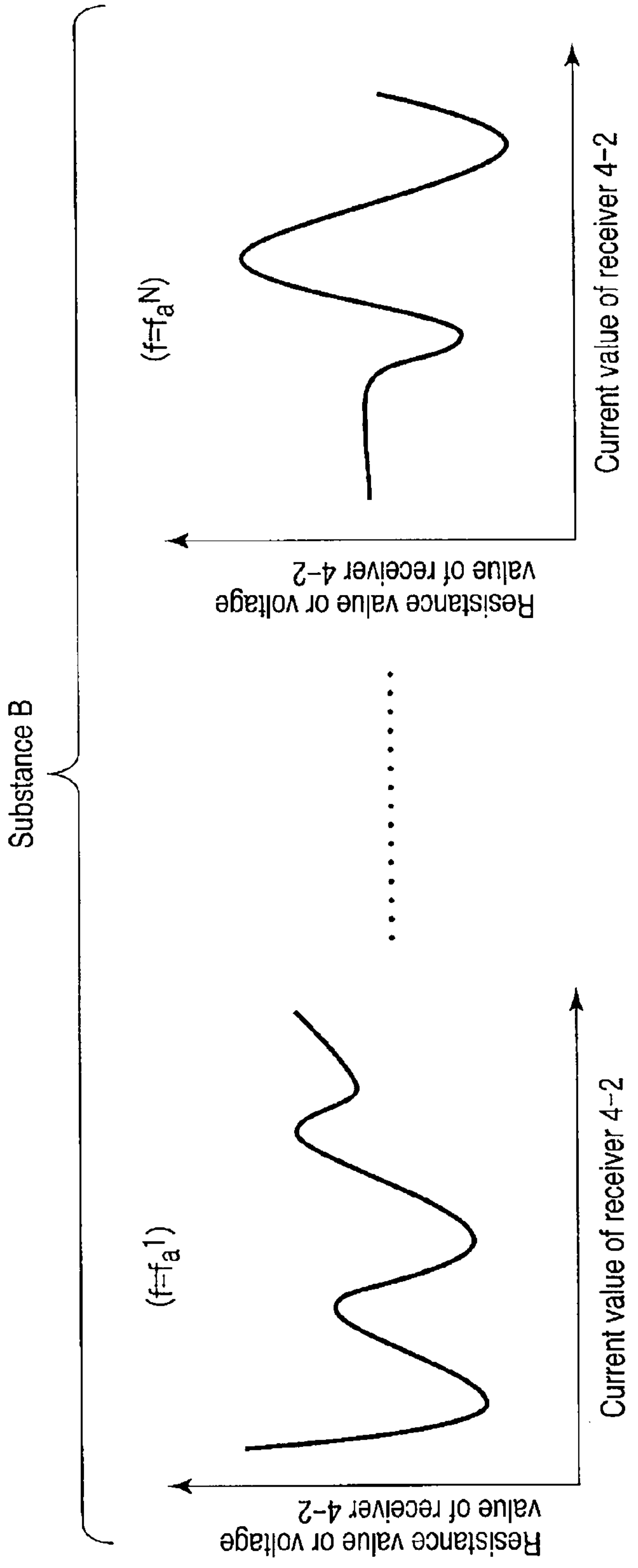
FIG. 6 illustrates graphs showing an example of detected data to be compared with dictionary data concerning a substance B which is detected by the receiver in correspondence with oscillation frequencies $f_a$1 to $f_a$N of waves oscillated by the oscillator in the specimen identification system shown in FIG. 1.

In the above-described detection, the value of the current supplied to the oscillator 4-1 is continuously changed. This enables to measure the change in the transmission characteristic of the specimen 12 based on the change in the oscillation frequency of the oscillator 4-1. That is, the oscillation frequency of the oscillator 4-1 is fixed, and the frequency of the receiver 4-2 is scanned in this state, thereby detecting the information of the specimen. The data is prepared in advance by measurement. The frequency characteristic of each specimen 12 is held in a nonvolatile memory 38 of the testing system as dictionary data. Data as shown in FIGS. 5 and 6, which are obtained from the specimen 12 for substances A and B, are collated with the dictionary data, thereby identifying the specimen 12. That is, since the transmission characteristic changes depending on the frequency, the specimen 12 can be specified and identifyd.

FIGS. 5 and 6 show data detected by the receiver 4-2 when the substances A and B are the test targets. The detected data changes between the substances A and B. For this reason, collating these data with the dictionary data allows to identify the substances A and B. The data graphs shown in FIGS. 5 and 6 are prepared for the receiver 4-2 as many as the number of frequencies $f_a$1 to $f_a$N changing in the oscillator 4-1. That is, a THz wave having the frequency $f_a$1 is output from the oscillator 4-1 and irradiates the specimen 12. During this time, the current supplied to the receiver 4-2 is swept, and the change in the resistance value or voltage value of the receiver 4-2 is detected. Similarly, a THz wave having the frequency $f_a$N is output from the oscillator 4-1 and irradiates the specimen 12. During this time, the current supplied to the receiver 4-2 is swept, and the change in the resistance value or voltage value of the receiver 4-2 is detected.

Hence, FIGS. 5 and 6 illustrate the graphs of the change in the resistance value or voltage value (ordinate) of the receiver 4-2 with respect to the current (abscissa) flowing to the receiver 4-2 for the N frequencies $f_a1$ to $f_aN$. The data shown in FIGS. 5 and 6 are referred to for a more detailed specimen identification operation to be described later so as to foster better understanding.

As shown in FIG. 1, in the specimen identification system, to operate the oscillator 4-1 and the receiver 4-2, they are connected to the variable power supplies 14-1 and 14-2, respectively. Powers supplied from the variable power supplies 14-1 and 14-2 to the oscillator 4-1 and the receiver 4-2 are synchronously controlled in accordance with a control signal from the power supply control circuit 32. An oscillation control signal from the oscillation control unit of the power supply control circuit 32 is supplied to the variable power supply 14-1. The variable power supply 14-1 sweeps the oscillation frequency of the THz wave to be oscillated from the oscillator 4-1 within a band, thereby operating the oscillator 4-1 to generate the THz wave. A detection control signal from the detection control unit of the power supply control circuit 32 is supplied to the variable power supply 14-2. The variable power supply 14-2 sweeps the oscillation frequency of the THz wave to be detected by the detector 4-2 within the band, thereby operating the detector 4-2 to generate a detection signal.

A voltage is applied between the lower electrode 26 and the upper electrode 28 of the oscillator 4-1 in accordance with the control signal from the power supply control circuit 32 under the control of an arithmetic and control unit (CPU) 40 so as to inject a current to the oscillator 4-1. Upon this current injection, the oscillator 4-1 outputs a wave having a THz oscillation frequency. Under the control of the arithmetic and control unit (CPU) 40, the current flowing to the oscillator 4-1 is converted into a detected current signal by an interface 34 and temporarily stored in a memory 36. The arithmetic and control unit (CPU) 40 converts the detected current signal into an oscillation frequency corresponding to the detected current by looking up the dictionary data in the nonvolatile memory 38 and stores it in the memory 36.

The voltage applied to the oscillator 4-1 changes so as to rise or fall stepwise. The frequency of the wave output from the oscillator 4-1 changes in accordance with the voltage change. The detection signal of the current flowing to the oscillator 4-1 also changes stepwise. The value of the oscillation frequency stored in the memory 36 also changes in accordance with the change in the detection signal. The value of the oscillation frequency is stored in the memory 36 in association with the resistance detection signal from the receiver 4-2.

For the receiver 4-2 as well, a current is supplied from the lower electrode 26 to the upper electrode 28 of the oscillator 4-1 in accordance with the control signal from the power supply control circuit 32 under the control of the arithmetic and control unit (CPU) 40 so as to maintain the oscillator 4-1 in the operative state. In this state, a wave having a THz oscillation frequency is introduced from the oscillator 4-1 to the receiver 4-2. Under the control of the arithmetic and control unit (CPU) 40, the voltage of the receiver 4-2 is converted into a detected voltage signal by the interface 34 and temporarily stored in the memory 36. The arithmetic and control unit (CPU) 40 may convert the detected voltage signal into the internal resistance of the receiver 4-2 and store it in the memory 36. The current supplied into the oscillator 4-1 changes so as to rise or fall stepwise in synchronism with the change in the current or voltage applied to the oscillator 4-1. The value of the current or voltage supplied to the oscillator is physically associated with the THz oscillation frequency and therefore stored in the memory 36 as a fundamental parameter to acquire the frequency spectrum of the specimen.

As already described, when the specimen 12 is irradiated with the THz wave corresponding to the natural frequency of the molecules of the specimen 12, the wave is modulated. When the modulated wave is introduced into the receiver 4-2, the internal resistance or the detected voltage signal changes. The change in the internal resistance or the detected voltage signal is also stored in the memory 36 in association with the THz oscillation frequency.

The memory 36 stores the change in the oscillation frequency oscillated by the oscillator 4-1 and the change in the internal resistance or the detected voltage signal. The stored changes in the oscillation frequency and the internal resistance or the detected voltage signal are unique to the specimen 12. Hence, the oscillation frequency of each substance and the change in the internal resistance or detected voltage signal of the receiver for each oscillation frequency in correspondence with the current supplied to the receiver are stored in advance as the dictionary data in the nonvolatile memory 38. For example, the acquired data which relates to the substances A and B are independently changed as shown in FIGS. 5 and 6. For this reason, collating these data with the dictionary data allows to identify the substance of the specimen 12.

The memory 36, the nonvolatile memory 38, and the arithmetic and control unit (CPU) 40 described above constitute a specimen identification unit that specifies the specimen based on the waveform of the detection signal in the frequency band.

As described above, to uniquely identify the specimen 12, it is necessary to acquire the transmission or reflection frequency spectrum data of the specimen 12 in advance and store them in the nonvolatile memory 38 as dictionary data. Detected frequency spectrum data is collated with the dictionary data of the database prepared in advance, thereby identifying the specimen 12. That is, it is possible to determine the substance of the specimen 12 by collating the detected frequency spectrum data with the dictionary data. More specifically, fingerprint spectrum identification of the specimen 12 is done using THz light, thereby identifying the specimen 12 based on the fact that the natural frequency at the molecular level falls within the frequency domain.

Note that using the oscillator 4-1 and the receiver 4-2 each including a magnetic multilayered film makes it possible to arrange the oscillator 4-1 and the receiver 4-2 on the single substrate 6 on which the specimen 12 is arranged and thus perform specimen identification using a THz wave at an extremely low cost. Since the oscillator, the receiver, and the specimen are arranged on the single substrate, a compact and inexpensive biosensor can be implemented.

Note that the current to the receiver 4-2 changes so as to change the frequency of the receiver 4-2 by referring to FIGS. 5 and 6. In a simpler system, a constant current may be supplied to the receiver 4-2 to fix the frequency. In this system, measurement can be done at the frequency set in the receiver 4-2 for the sweep frequency from the oscillator 4-1. Such a system is used to detect a specific substance. That is, in the general form described in the above embodiment, the frequency of the receiver 4-2 is scanned and changed in correspondence with one frequency of the oscillator 4-1. Depending on the circumstances, an embodiment in which scanning the frequency of the receiver 4-2 is omitted may be possible.

The identification procedure or sequence of the specimen identification system shown in FIG. 1 will be explained with reference to the flowchart of FIG. 7.

When the identification procedure starts, the test specimen 12 is arranged in the channel 8 on the sensor chip shown in FIG. 2 (step S10). The specimen 12 can be a liquid such as blood, saliva, or sweat, or such a liquid collected from a human body and undergone component separation. In case of a liquid, the test specimen 12 may be arranged on the chip and then held in the channel in the region to be irradiated with the oscillation signal. Alternatively, the test specimen 12 may be arranged on the chip and then moved on the chip as a liquid by a moving mechanism up to the region on the channel to be irradiated with the oscillation signal. The specimen need not always be a liquid but may be a solid. If the specimen is a solid, the test specimen 12 is arranged in the region to be irradiated with the oscillation signal, as a matter of course.

Next, one oscillation condition is set, and a wave from the oscillator 4-1 irradiates the test specimen 12 (step S12). The oscillated wave may directly irradiate the specimen 12. Alternatively, the oscillated wave may be reflected in the device to indirectly irradiate the specimen 12. In both direct irradiation and indirect irradiation, the arrangement of the oscillator 4-1 and the receiver 4-2 needs to be adjusted to irradiate the test specimen 12 with the oscillated wave.

In the state in which the test specimen 12 is irradiated with the oscillated wave, the internal resistance, the voltage value, the current value or the like of the receiver 4-2 is measured and stored in the memory 36.

At this time, to most efficiently detect the information of the wave transmitted through or reflected by the specimen, the current value of the receiver is changed to change its oscillation condition, and then, data is acquired (step S14).

The oscillator 4-1 is caused to oscillate under a changed oscillation condition (step S16). Since the test specimen 12 is already arranged on the chip, the signal of the different oscillation condition irradiates the test specimen 12. Detailed examples of the condition to be changed are the current value of the oscillator 4-1 and the magnitude of the magnetic field to be applied to the oscillator 4-1.

In the state of step S16, the resistance, the voltage, the current value, or the like of the receiver 4-2 is measured, and the measured data is stored in the memory 36, as in step S14. At this time, the current value of the receiver is changed to change its oscillation condition, and then, data is acquired, as in step S14 (step S18).

In step S19 next to step S18, steps S16 and S18 are repeated a necessary number of times to acquire data a necessary number of times. The reception characteristic for the oscillation frequency of the oscillator 4-1 is measured by repeating steps S16 and S18. That is, frequency spectrum data is acquired.

When the measurement in steps S16 and S18 is repeated the necessary number of times, the process advances to step S20. The data obtained by the measurement in steps S16 and S18 are organized as spectrum data in the form of data dependence on the oscillator 4-1 upon changing the oscillation condition. Physically, the condition dependence of the oscillator 4-1 corresponds to the frequency dependence of the oscillator 4-1. The parameter that is actually changed experimentally normally corresponds to the current value dependence of the oscillator 4-1. However, when the magnetic field applied to the oscillator 4-1 is changed, the parameter may be the external magnetic field dependence. As the characteristic of the receiver 4-2, a resistance value, that is, a voltage measurement value for a sense current value is normally acquired as data.

Next, the data organized in step S20 is collated or compared with the dictionary data already held on the device side (step S21). Since the collation reveals that the substance has unique fingerprint spectrum data, the substance can uniquely be identified.

The same data as shown in FIGS. 5 and 6 are acquired in advance by experiments using an experimental system that is almost the same as identification device shown in FIG. 2, and stored in the nonvolatile memory 38 shown in FIG. 1. The dictionary data is collated with the measured data, thereby identifying the specimen.

An supplementary description will be made below on details of the oscillator 4-1 and the receiver 4-2 described in the various aforementioned embodiments, and various examples thereof will be described.

As each of the oscillator 4-1 and the receiver 4-2, a spin torque oscillator having a CCP-CPP structure is used, as already described.

The oscillator and the receiver are preferably supposed to have almost the same structure because they are basically viewed in the same frequency domain. When a wave is radiated from the oscillator to the specimen 12 and transmitted through the specimen 12, a frequency shift occurs. For this reason, the frequency detected by the receiver does not necessarily match the frequency of the oscillator. However, since the frequency shift caused upon passage through the specimen 12 is supposed to be not so large, almost the same structure can be used as the oscillator 4-1 and the receiver 4-2.

The device structure of the oscillator 4-1 or the receiver 4-2 is not limited to that shown in FIG. 3. Various arrangement structures shown in FIGS. 8A, 8B, 8C, 8D, and BE may be adopted.

In a stacked structure according to an example shown in FIG. 8A, a spacer layer S corresponding to the intermediate layer 22 is provided between a first magnetic layer F1 corresponding to the magnetic layer 20 and a second magnetic layer F2 corresponding to the magnetic layer 24, like the structure shown in FIG. 3. Nano-size current confined portions corresponding to the nano-size current paths 22P are provided in the spacer layer S so that the spacer layer S has the function of a nano-size current path layer X. Without power supply, magnetization in the first magnetic layer F1 and the second magnetic layer F2 occurs in the directions indicated by the arrows in FIG. 8A. The current confined in the current paths 22P of the spacer layer S attains a high current density in the first magnetic layer F1 and the second magnetic layer F2.

In a structure according to an example shown in FIG. 8B, the nano-size current path layer X having the nano-size current confined portions 22P is provided on the second magnetic layer F2, and the spacer layer S is provided between the first magnetic layer F1 and the second magnetic layer F2. Without power supply, magnetization in the first magnetic layer F1 and the second magnetic layer F2 occurs in the directions indicated by the arrows in FIG. 8B. In the structure shown in FIG. 8B, the spacer layer S and the nano-size current path layer X are separately provided. In the structure shown in FIG. 8B, the current is confined in the nano-size current path layer X and then confined to the nanometer order in the second magnetic layer F2.

Figure 8C:
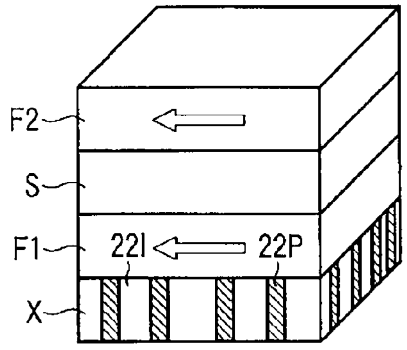
FIG. 8C is a perspective view schematically showing still another example of the device structure shown in FIG. 3.

In a structure according to an example shown in FIG. 8C, the nano-size current path layer X having the nano-size current confined portions 22P is provided under the first magnetic layer F1, and the spacer layer S is provided between the first magnetic layer F1 and the second magnetic layer F2. Without power supply, magnetization in the first magnetic layer F1 and the second magnetic layer F2 occurs in the directions indicated by the arrows in FIG. 8C. In the structure shown in FIG. 8C, the spacer layer S and the nano-size current path layer X are separately provided, as in FIG. 8B. In the structure shown in FIG. 8C, the current is confined in the nano-size current path layer X and then confined to the nanometer order in the first magnetic layer F1.

Figure 8D:
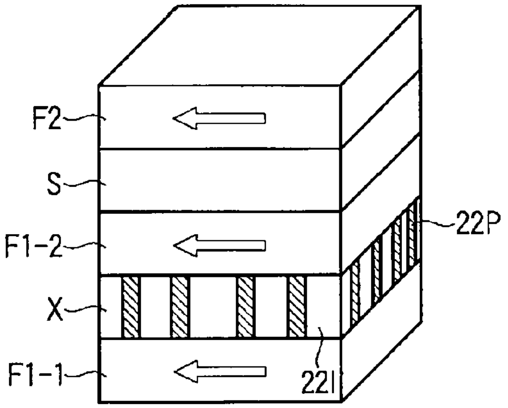
FIG. 8D is a perspective view schematically showing yet another example of the device structure shown in FIG. 3.

In a structure according to an example shown in FIG. 8D, the first magnetic layer F1 is divided into two magnetic layers F1-1 and F1-2. The nano-size current path layer X is arranged between the two magnetic layers F1-1 and F1-2. The spacer layer S is provided between the first magnetic layer F1-2 and the second magnetic layer F2. Without power supply, magnetization in the first magnetic layers F1-1 and F1-2 and the second magnetic layer F2 occurs in the directions indicated by the arrows in FIG. 8D. In the structure shown in FIG. 8D, the spacer layer S and the nano-size current path layer X are separately provided, as in FIGS. 8B and 8C. In the structure shown in FIG. 8D, the current is confined in the nano-size current path layer X and then confined to the nanometer order in the first magnetic layers F1-1 and F1-2.

Figure 8E:
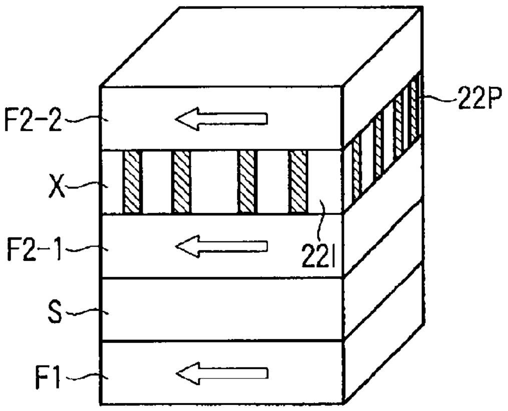
FIG. 8E is a perspective view schematically showing yet still another example of the device structure shown in FIG. 3.
Figure 9A:
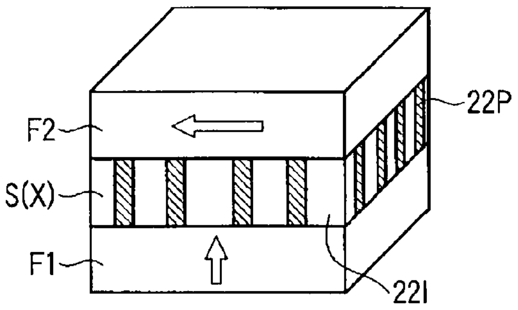
FIG. 9A is a perspective view schematically showing a modification of the device structure shown in FIG. 8A.
Figure 9B:
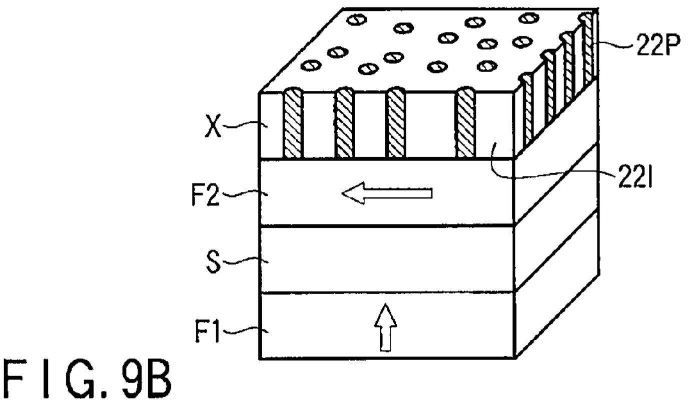
FIG. 9B is a perspective view schematically showing a modification of the device structure shown in FIG. 8B.
Figure 9C:
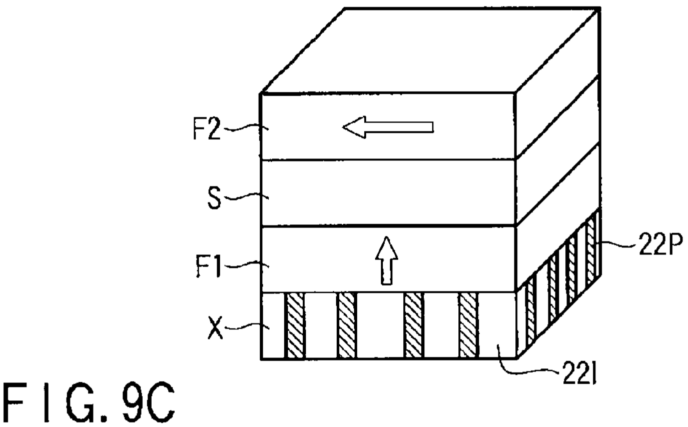
FIG. 9C is a perspective view schematically showing a modification of the device structure shown in FIG. 8C.
Figure 9D:
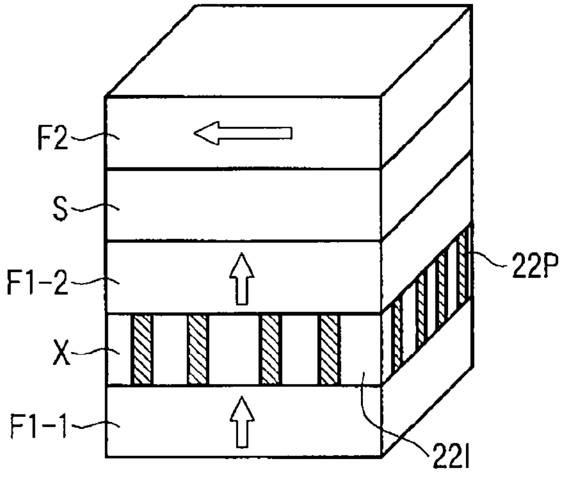
FIG. 9D is a perspective view schematically showing a modification of the device structure shown in FIG. 8D.
Figure 9E:
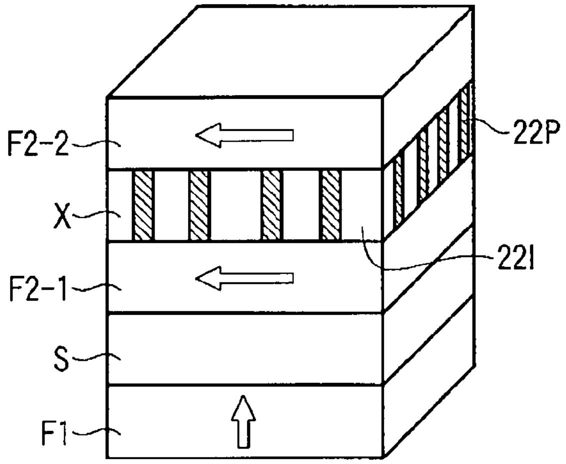
FIG. 9E is a perspective view schematically showing a modification of the device structure shown in FIG. 8E.
Figure 10A:
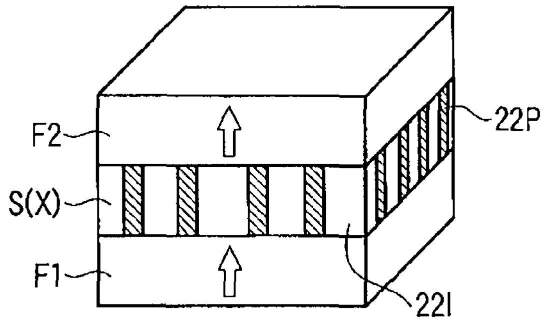
FIG. 10A is a perspective view schematically showing another modification of the device structure shown in FIG. 8A.
Figure 10B:
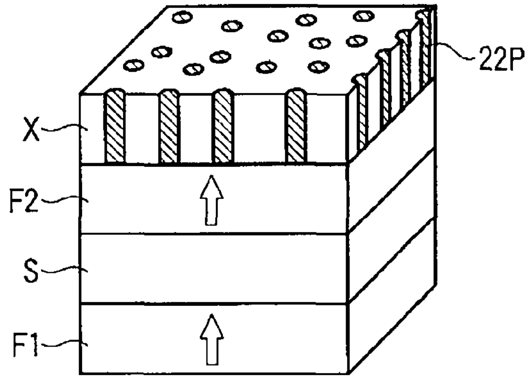
FIG. 10B is a perspective view schematically showing another modification of the device structure shown in FIG. 8B.
Figure 10C:
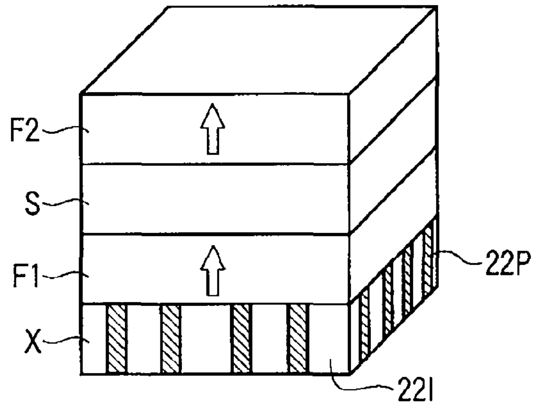
FIG. 10C is a perspective view schematically showing another modification of the device structure shown in FIG. 8C.

In a structure according to an example shown in FIG. 8E, the second magnetic layer F2 is divided into two magnetic layers F2-1 and F2-2. The nano-size current path layer X is arranged between the two magnetic layers F2-1 and F2-2. The spacer layer S is provided between the first magnetic layer F1 and the second magnetic layer F2-1. Without power supply, magnetization in the first magnetic layer F1 and the second magnetic layers F2-1 and F2-2 occurs in the directions indicated by the arrows in FIG. 8E. In the structure shown in FIG. 8E, the spacer layer S and the nano-size current path layer X are separately provided, as in FIGS. 8B, 8C, and 8D. In the structure shown in FIG. 8E, the current is confined in the nano-size current path layer X and then confined to the nanometer order in the second magnetic layers F2-1 and F2-2.

Even in the structures shown in FIGS. 8A, 8B, 8C, 8D, and BE described above, the current supplied from one of the upper electrode 28 and the lower electrode 26 to the magnetic multilayered film in the direction perpendicular to the film planes is confined in the plurality of nano-size current paths 22P of the nano-size current path layer X and flowed toward the other electrode to generate a THz wave. It is therefore possible to efficiently cause high-frequency oscillation by spin torque.

In the structures according to the examples shown in FIGS. 8A, 8B, 8C, 8D, and BE described above, magnetization in the first magnetic layers F1 F1-1, and F1-2 and the second magnetic layers F2, F2-1, and F2-2 occurs in the direction parallel to the film planes. However, as shown in FIGS. 9A, 9R, 9C, 9D, and 9E, magnetization in the second magnetic layers F2, F2-1, and F2-2 may occur in the direction parallel to the film planes, as in the structures shown in FIGS. 8A, 8B, 8C, 8D, and 8E, whereas magnetization in the first magnetic layers F1, F1-1, and F1-2 may occur in the direction perpendicular to the film planes. As shown in FIGS. 10A, 10B, 10C, 10D, and 10E, magnetization in the first magnetic layers F1 F1-1, and F1-2 and the second magnetic layers F2, F2-1, and F2-2 may occur in the direction perpendicular to the film planes. The structures shown in FIGS. 9A, 9B, 9C, 9D, 9E, 10A, 10B, 10C, 10D, and 10E are the same as those shown in FIGS. 8A, 8B, 8C, 8D, and BE except the direction of magnetization. Hence, the same reference numerals denote the same parts, and a description thereof will be omitted.

In the structures shown in FIGS. 3, 8A, 8B, 8C, 8D, 8E, 9A, 9R, 9C, 9D, 9E, 10A, 10B, 10C, 10D, and 10E, the single intermediate layer 22 or the single nano-size current path layer X is provided. However, a plurality of nano-size current path layers X may be provided, and the nano-size current paths 22P may be provided in each nano-size current path layer X to confine the current at the plurality of portions.

Figure 11:
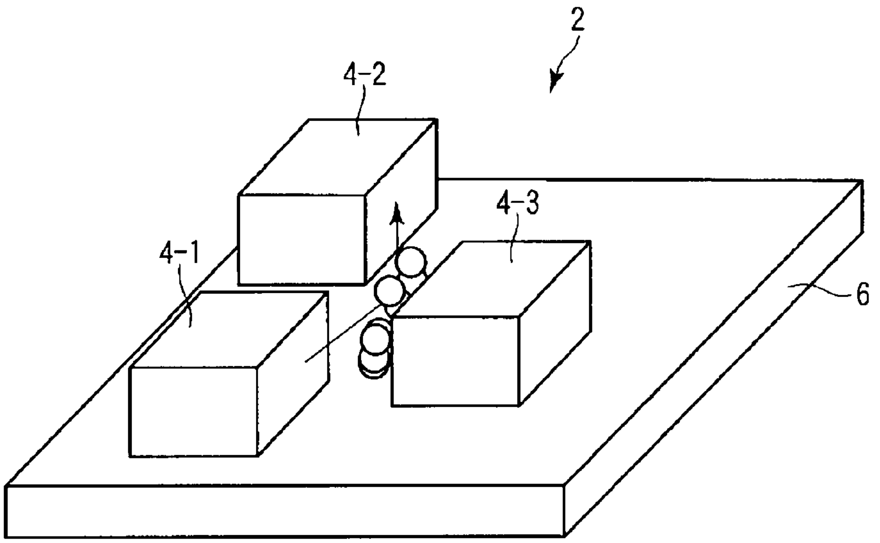
FIG. 11 is a perspective view schematically showing a reflection detection type specimen identification device shown in FIG. 1.

As shown in FIG. 11, the specimen identification device 2 may be configured to detect not a wave transmitted through the specimen 12, as already described, but a wave reflected by the specimen 12. In the device 2 shown in FIG. 11, a reflector 4-3 is arranged to face the oscillator 4-1 and the receiver 4-2 so that the wave generated by the oscillator 4-1 is reflected by the reflector 4-3 and directed to the receiver 4-2. In this arrangement, the receiver 4-2 measures a reflection spectrum generated when the specimen 12 reflects the wave in place of an absorption spectrum generated when the specimen 12 absorbs the wave, unlike the arrangement shown in FIG. 1. In this arrangement, the reflector 4-3 is made of a material to reflect the THz wave and arranged on the rear side of the specimen 12 on the side opposite to the oscillator 4-1 and the receiver 4-2.

Figure 12:
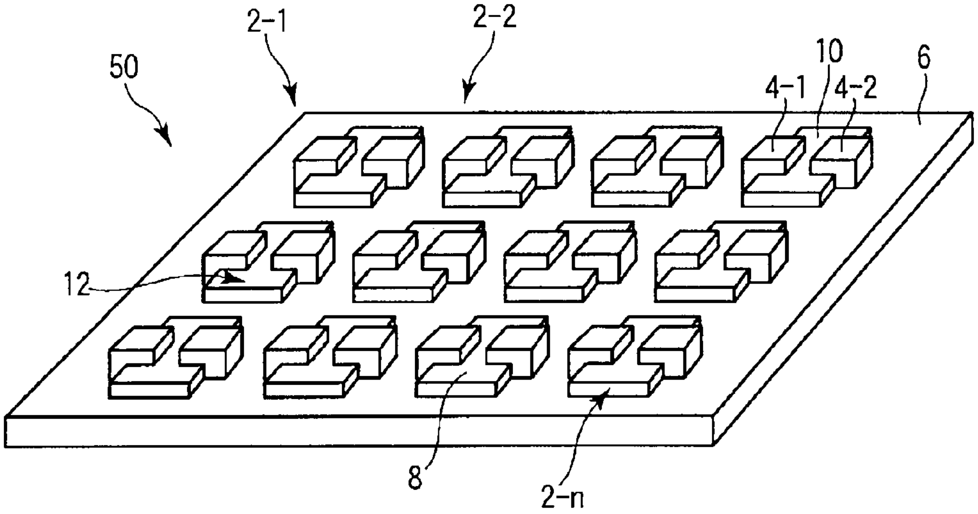
FIG. 12 is a perspective view schematically showing a specimen identification device array in which the specimen identification devices shown in FIG. 1 are arranged in an array.

FIG. 12 illustrates a specimen identification device array. In the specimen identification device array shown in FIG. 12, detection devices 2-1 to 2-*n* each including a pair of the oscillator 4-1 and the receiver 4-2 are arranged in an array, for example, in a matrix on the substrate 6. The specimen identification device array is connected to the variable power supplies 14-1 and 14-2 controlled by the power supply control circuit 32 and also connected to the arithmetic processing unit 40 and the memory 36 via the interface, as in FIG. 1. The channels 8 of the detection devices 2-1 to 2-*n* may be separated from each other or communicate to each other. In the structure having the channels 8 separated from each other, the single specimen 12 may be allocated to each channel 8. In the structure having the channels 8 communicating to each other, the specimen 12 may be given and allocated externally, or flow among the channels 8 and allocated to each of them.

In the array shown in FIG. 12, the oscillators 4-1 of the detection devices 2-1 to 2-*n* generate waves having THz frequencies in bands different from each other so that the THz frequencies in the different bands cover a wide THz frequency band. In addition, the receivers 4-2 of the detection devices 2-1 to 2-*n* operate to detect the THz frequencies in the bands different from each other, thereby generating a detection signal. The THz frequencies in the wide band can therefore simultaneously be detected by the THz frequencies in the different bands. Hence, when the specimen 12 is allocated to each channel 8, and the detection devices 2-1 to 2-*n* operate, the specimen 12 can be specified by detecting the absorption spectra of the specimen 12 in the wide THz frequency band based on the signals from the detection devices 2-1 to 2-*n*. That is, detection data as shown in FIG. 7A or 7B can be obtained without needing frequency sweep in the oscillator 4-1 or current or voltage sweep in the receiver 4-2.

Note that the structural design of the dimensions and the like of each portion of the oscillator 4-1 and the receiver 4-2 may be changed. Instead of allocating the single specimen to each channel 8, a plurality of different specimens 12 may be allocated to the different channels 8 so that the plurality of detection devices 2-1 to 2-*n* on the single substrate 6 simultaneously identify the plurality of specimens 12. When detecting the plurality of specimens 12, frequency sweep, current sweep, or voltage sweep may be executed in the plurality of detection devices 2-1 to 2-*n*, as in the above-described embodiment.

FIG. 13 shows a device structure according to another embodiment, which comprises a mechanism for externally applying a magnetic field to a stacked structure 27 of an oscillator 4-1 or the stacked structure 27 of a receiver 4-2. In this device structure, the stacked structure 27 is arranged between a lower electrode 26 and an upper electrode 28. Hard magnetic layer films 54-1 and 54-2 having a large coercive force are arranged on both sides of the stacked structure 27.

Insulating films 52 intervene between the stacked structure 27 and the hard magnetic layer films 54-1 and 54-2 and between the hard magnetic layer films 54-1 and 54-2 and the lower electrode 26 and the upper electrode 28. The device structure comprising the hard magnetic layer films 54-1 and 54-2 can stably apply a magnetic field to the stacked structure 27 and thus implement stable oscillation.

In the device structures shown in FIGS. 3 and 13, the upper electrode 28 and the lower electrode 26 are arranged on and under the stacked structure 27. However, the first electrode 26 and the second electrode 28 may be arranged on both sides of the stacked structure 27, as shown in FIG. 14. The device structures shown in FIGS. 3 and 13 are called a current-perpendicular-to-plane type which injects a current perpendicularly to the film planes of the stacked structure 27 to generate spin torque. The device structure shown in FIG. 14 is called a current-in-plane type which generates spin torque by a current flowing along the film planes of the stacked structure 27. The oscillator 4-1 and the receiver 4-2 may be formed into the current-in-plane type.

FIG. 15 shows a modification of the device structure of the current-in-plane type shown in FIG. 14. In the device structure shown in FIG. 15, hard magnetic members 56-1 and 56-2 for applying a magnetic field to the stacked structure 27 are arranged on both sides of the stacked structure 27. The first electrode 26 and the second electrode 28 are arranged on the hard magnetic members 56-1 and 56-2, respectively. In this structure as well, a current is supplied in parallel to the film planes of the stacked structure from one of the first electrode 26 and the second electrode 28 to the other of the first electrode 26 and the second electrode 28 via the hard magnetic members 56-1 and 56-2. The magnetic field is stably externally applied to the stacked structure 27, and the current flows in the stacked structure 27, thereby generating spin torque.

FIGS. 16A, 16B, and 16C show the planar shapes of an oscillator 4-1 or a receiver 4-2 according to still another embodiment. In the structure shown in FIG. 16A, a single layer film structure 60 is formed on a substrate 6. Both sides of the single layer film structure 60 are respectively connected to a first electrode 26 and a second electrode 28 which supply a current to the single layer film structure 60. In the single layer film structure 60, a first magnetic layer 58-1 and a second magnetic layer 58-2 are buried in an insulating layer 62. The first magnetic layer 58-1 and the second magnetic layer 58-2 extend from the first electrode 26 and the second electrode 28, respectively. Distal ends 58A and 58B are tapered so as to gradually decrease the width. The tapered ends are connected to each other at a pinpoint. When the first magnetic layer 58-1 and the second magnetic layer 58-2 are formed, the current flowing through them is confined into a nanocurrent at the tapered distal ends 58A and 58B to generate spin torque. The structure shown in FIG. 16A can be formed flat on the substrate. Hence, a detection device comprising the oscillator 4-1 and the receiver 4-2 adopting the structure can have a flat structure. This allows to make the sensor compact and flat.

If it may be impossible to expect generation of a wave having a sufficient intensity in the structure shown in FIG. 16A, an array structure as shown in FIG. 16B or 16C may be formed. In the structure shown in FIG. 16B, the single layer film structure 60 is similarly formed on the substrate 6. Both sides of the single layer film structure 60 are respectively connected to the first electrode 26 and the second electrode 28 which supply a current to the single layer film structure 60. In the single layer film structure 60, a plurality of first magnetic layers 58-1 are buried in the insulating layer 62 almost parallel to each other. Similarly, a plurality of second magnetic layers 58-2 are buried in the insulating layer 62 almost parallel to each other. The first magnetic layers 58-1 and the second magnetic layers 58-2 extend from the first electrode 26 and the second electrode 28, respectively. The distal ends 58A and 58B are tapered so as to gradually decrease the width. The tapered ends are connected to each other at a pinpoint. When a number of first magnetic layers 58-1 and a number of second magnetic layers 58-2 are formed in parallel, the current flowing through them is confined into a nanocurrent at a number of tapered distal ends 58A and 58B to generate spin torque at a plurality of portions. Like the structure shown in FIG. 16A, the structure shown in FIG. 16B can be formed flat on the substrate. Hence, a detection device comprising the oscillator 4-1 and the receiver 4-2 adopting the structure can have a flat structure. This allows to make the sensor compact and flat.

In the array structure shown in FIG. 16C, the tapered distal ends 58A and 58B, which are connected to each other in the array structure shown in FIG. 16B, are connected via a nonmagnetic layer segment 64. In this structure, a nano-size current path portion a nanocurrent passes through is formed from the nonmagnetic layer segment 64. The current is confined into a nanocurrent in the nonmagnetic layer segments 64 serving as the nano-size current path portions to generate spin torque at a plurality of portions. Like the structure shown in FIG. 16B, the structure shown in FIG. 16C can be formed flat on the substrate. Hence, a detection device comprising the oscillator 4-1 and the receiver 4-2 adopting the structure can have a flat structure. This allows to make the sensor compact and flat.

In the structures shown in FIGS. 16A, 16B, and 16C, the single layer film structure 60 is formed. It is obvious that the single layer film structures 60 may be stacked while inserting insulating layers between them and connected to the first electrode 26 and the second electrode 28.

As shown in FIGS. 17A and 17B, wiring lines 70-1 and 70-2 may be provided in the oscillator 4-1 or the receiver 4-2 to apply an external magnetic field to the oscillator 4-1 or the receiver 4-2.

In the structure according to the example shown in FIG. 17A, the wiring lines 70-1 and 70-2 for applying a current magnetic field run in a direction perpendicular to the film planes of the stacked structure 27. Currents flow to the wiring lines 70-1 and 70-2 in the directions of the arrows so as to form variable magnetic fields circumferentially around them. The variable magnetic fields are formed depending on the currents flowing to the wiring lines 70-1 and 70-2. As a result, the variable magnetic fields enter the stacked structure 27 from its side surfaces along the films to magnetize magnetic layers 20 and 24. Hence, spin torque generated in the stacked structure 27 depends on the given variable magnetic fields.

Note that in FIG. 17A, two wiring lines are used while setting opposite current directions, thereby making the direction of a magnetic field applied to the device constant. However, the number of wiring lines need not always be two. One wiring line may suffice. In addition, a magnetic material (not shown) may be formed around each wiring line for applying a magnetic field to strengthen the magnetic field.

In the structure according to the example shown in FIG. 17B, the wiring lines 70-1 and 70-2 for applying a current magnetic field run along a direction parallel to the film planes of the stacked structure 27. Currents flow to the wiring lines 70-1 and 70-2 in the directions of the arrows so as to form magnetic fields circumferentially around them. As a result, the magnetic fields similarly enter the stacked structure 27 from its side surfaces along the films to magnetize the magnetic layers 20 and 24.

Figure 18:
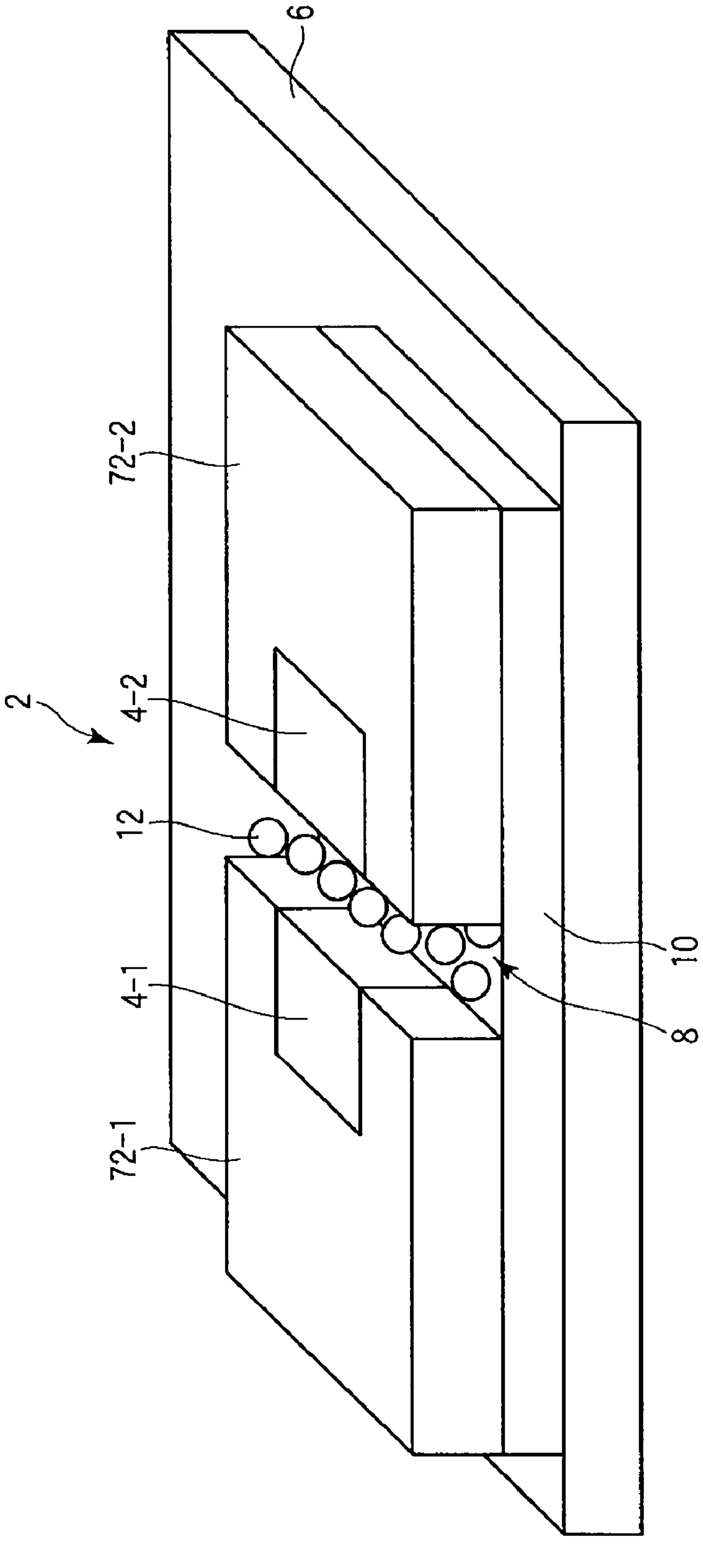
FIG. 18 is a perspective view schematically showing the structure of a specimen identification device shown in FIG. 2 according to another embodiment.

FIG. 18 illustrates a preferable modification of the specimen identification device 2 shown in FIG. 2. In the specimen identification device 2, the side surfaces of the oscillator 4-1 and the receiver 4-2 except the surfaces facing the channel 8 are surrounded by shields 72-1 and 72-2 configured to shield a THz wave. Hence, the oscillator 4-1 and the receiver 4-2 are shielded not to be affected by the ambient environment.

Note that insulating layers (not shown) preferably intervene between the shields 72-1 and 72-2 and the oscillator 4-1 and the receiver 4-2 to prevent current leakage.

Figure 19:
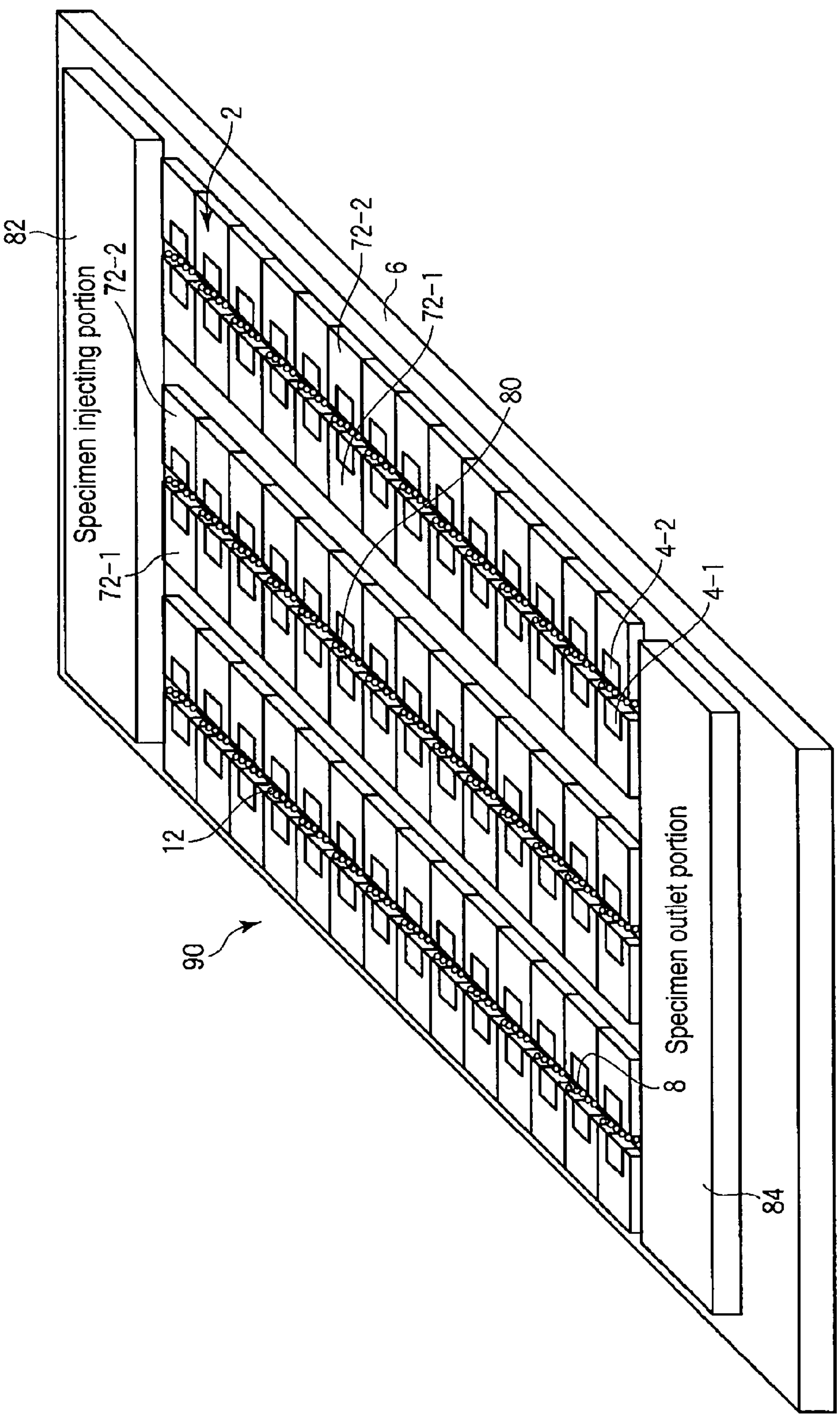
FIG. 19 is a perspective view schematically showing a chip structure in which a number of specimen identification devices shown in FIG. 18 are arrayed.

As shown in FIG. 19, a specimen identification chip 90 is preferably formed by arraying a number of specimen identification devices 2 shown in FIG. 18 in a plurality of lines on the substrate 6. The specimen identification chip may be configured such that a specimen channel 80 is formed by the linearly arranged channels 8 of the specimen identification devices 2, and a specimen 12, for example, a specimen mixed into a solution is injected from one of specimen injecting portions 82 and 84 and flowed toward the other of the specimen injecting portions 82 and 84.

A lid (not shown) covers the upper surface of the specimen identification chip 90 to seal the specimen channel 80. One or both of the specimen injecting portions 82 and 84 are filled with the specimen 12. Each of the injecting portions 82 and 84 has a gate to flow the specimen into the specimen channel 80 at the start of test. The specimen channel 80 may tilt to naturally flow the solution containing the specimen 12 through it. The specimen identification chip may be configured to cause a supply mechanism (not shown) to circulate the solution containing the specimen 12 through the specimen channel 80.

The specimen identification chip 90 shown in FIG. 19 can operate to obtain detection data like the specimen identification device array shown in FIG. 12.

Note that in the structure that covers the upper surface of the specimen identification chip 90 by a lid, the specimen channel 80 may be not only sealed but also kept vacuum inside. The specimen injecting portions 82 and 84 may also be sealed and kept vacuum inside. The specimen identification chip 90 may be configured such that the injecting portion of a specimen injecting tool (not shown) (a sample holder that holds the specimen 12) having an injecting portion, such as a syringe with an injection needle, is inserted into one of the specimen injecting portions 82 and 84 so as to supply the specimen 12 into the specimen identification chip 90 while keeping the specimen shielded from the outside air.

Even the specimen identification devices shown in FIGS. 2, 11, 12, and 20A are preferably formed into a capsule structure in which the channel 8 is sealed and kept vacuum. More preferably, a specimen injecting tool (not shown) supplies the specimen 12 to the channel 8 in the capsule structure while keeping the specimen 12 shielded from the external environment.

The structure preferably maintains the capsule vacuum to minimize attenuation of THz waves outside the sample because they attenuate in the atmosphere. The capsule kept vacuum has a negative pressure. Hence, when injecting the specimen 12 using an injection needle or the like, the specimen 12 serving as a sample enters the channel. Preferably, a rubber region is provided in advance on the capsule to facilitate insertion of the injection needle and inject the specimen 12 without breaking the vacuum while maintaining the vacuum or maintaining the negative pressure lower than the atmospheric pressure.

In the above-described various embodiment, to change the oscillation frequency of the oscillator 4-1 and the frequency to be detected by the receiver 4-2, the current supplied to the oscillator 4-1 or the receiver 4-2 is changed. However, as shown in FIGS. 20A and 20B, magnetic applying portions for applying magnetic fields to the oscillator 4-1 and the receiver 4-2 may be provided and adjusted to change the magnitudes of the applied magnetic fields.

FIGS. 20A and 20B illustrate a specimen identification device according to still another embodiment in which a receiver 4-2 and an oscillator 4-1 each comprising a magnet device for applying a magnetic field to the stacked structure are arranged on a substrate. In each of the receiver 4-2 and the oscillator 4-1, magnet devices 74-1 and 74-2 each serving as a magnetic applying portion for applying a magnetic field to a stacked structure 27 are arranged on both sides of the stacked structure 27, as shown in FIGS. 20A and 20B. Each of the magnet devices 74-1 and 74-2 need not always be formed from only a permanent magnet that generates a bias fixed magnetic field as shown in FIG. 13, but may include an electromagnet that generates a variable magnetic field based on a driving current from a driving circuit 76-1 or 76-2 using a permanent magnet as a yoke. In the magnet devices 74-1 and 74-2, not only the bias fixed magnetic field from the permanent magnet is applied to the stacked structure 27 but also the electromagnet is driven by the driving current from the driving circuits 76-1 and 76-2 to apply the variable magnetic field to the stacked structure 27. The variable magnetic field is increased or decreased by the driving current from the driving circuits 76-1 and 76-2. In the stacked structure, spin torque is generated by the increased or decreased variable magnetic field. This makes it possible to change the THz oscillation frequency to be generated by the oscillator and change the THz oscillation frequency to be detected by the receiver. Controlling the THz oscillation frequency by the variable magnetic field may be executed while maintaining a constant supplied current or applied voltage to the stacked structure 27, or in a state in which the supplied current or applied voltage to the stacked structure 27 is controlled, as in the embodiments already described above. More specifically, the magnet devices 74-1 and 74-2 may be the magnetic field wiring lines 70-1 and 70-2 shown in FIG. 17A or 17B. The external magnetic field to be applied to the stacked structure 27 by the current magnetic fields from the magnetic field wiring lines 70-1 and 70-2 may be changed by changing the values of currents to be supplied to the magnetic field wiring lines 70-1 and 70-2.

According to the specimen identification device of the present embodiment, it is possible to implement an oscillator capable of operating on a chip and oscillating a THz wave and allow to conduct a simple test to specify a specimen by the THz wave.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A specimen identification system comprising:
a device including
an oscillator generating a THz wave,
a channel comprising a waveguide and accommodating a specimen, the specimen being irradiated with the THz wave, and a receiver receiving the THz wave and generating a receiving signal, the THz wave being transmitted through the specimen or being reflected on the specimen;

a first controller controlling the oscillator to sweep an oscillation frequency of the THz wave within a frequency band;

a second controller controlling the receiver to sweep a receiving frequency of the THz wave within the frequency band; and a specimen identification unit that specifies the specimen based on a waveform of the receiving signal within the frequency band.

2. The specimen identification system according to claim 1, wherein the specimen identification unit includes:

a first memory unit that stores data of a receiving correlation graph that correlates the receiving signal with the frequency band;

a second memory unit that stores dictionary data of a lookup correlation graph having correlations between the frequency band and receiving signals concerning a plurality of known specimens; and a comparison operation circuit that compares the receiving correlation graph with the lookup correlation graph while looking up the dictionary data on the receiving correlation graph, thereby identifying the specimen.

3. The specimen identification system according to claim 1, wherein the second controller analyzes a resistance change in the receiver based on the receiving signal, and the specimen identification unit specifies the specimen based on the resistance change within the frequency band.

4. The specimen identification system according to claim 1, wherein the first controller controls a current to be supplied to the oscillator to sweep the oscillation frequency of the THz wave within a frequency band, and the second controller sweeps a current value to be supplied to the receiver to sweep the receiving frequency of the THz wave within the frequency band.

5. A specimen identification device comprising:

an oscillator generating a THz wave by sweeping an oscillation frequency of the THz wave within a frequency band;

a channel comprising a waveguide and accommodating a specimen, the specimen being irradiated with the THz wave; and a receiver provided so as to sandwich the channel with the oscillator and receiving the THz wave, the THz wave being transmitted through or being reflected on the specimen, the receiver generating a receiving signal by sweeping a receiving frequency of the THz wave within the frequency band.

6. The specimen identification device according to claim 5, wherein at least one of the oscillator and the receiver is formed from a device having a stacked film structure including a first magnetic layer, a second magnetic layer, and an intermediate layer arranged between the first magnetic layer and the second magnetic layer.

7. The specimen identification device according to claim 6, wherein the stacked film structure includes a high-frequency shift layer formed from an insulating layer and a plurality of current path layers extending through the insulating layer.

8. An integrated specimen identification apparatus wherein a plurality of specimen identification devices, each having a structure of the specimen identification device according to claim 5, are arranged on a single substrate.

9. The integrated specimen identification apparatus according to claim 8, wherein a shield portion that absorbs a wave in a terahertz region is provided between the specimen identification devices to prevent interference.

10. The integrated specimen identification apparatus according to claim 9, wherein the plurality of specimen identification devices have different oscillation frequency bands and different receiving frequency bands and cause the specimen identification units to specify a plurality of specimens.

* * * * *